(12) United States Patent
Pershadsingh

(10) Patent No.: US 7,232,828 B2
(45) Date of Patent: Jun. 19, 2007

(54) PPAR LIGANDS THAT DO NOT CAUSE FLUID RETENTION, EDEMA OR CONGESTIVE HEART FAILURE

(75) Inventor: Harrihar A. Pershadsingh, Bakersfield, CA (US)

(73) Assignee: Bethesda Pharmaceuticals, Inc., Mill Valley, CA (US)

( * ) Notice: Subject to any disclaimer, the term of this patent is extended or adjusted under 35 U.S.C. 154(b) by 166 days.

(21) Appl. No.: 10/627,372

(22) Filed: Jul. 24, 2003

(65) Prior Publication Data

US 2004/0127443 A1 Jul. 1, 2004

Related U.S. Application Data

(60) Provisional application No. 60/455,211, filed on Mar. 15, 2003, provisional application No. 60/402,425, filed on Aug. 10, 2002.

(51) Int. Cl.
*A61K 31/519* (2006.01)
(52) U.S. Cl. .................. 514/259.1; 541/258.1
(58) Field of Classification Search ........... 514/211.08, 514/218, 241, 242, 248, 255.5, 265.1, 266.21, 514/259.1, 258.1
See application file for complete search history.

(56) References Cited

U.S. PATENT DOCUMENTS

| | | |
|---|---|---|
| 5,128,356 A | 7/1992 | Naka et al. |
| 5,162,326 A | 11/1992 | Naka et al. |
| 5,196,444 A | 3/1993 | Naka et al. |
| 5,243,054 A | 9/1993 | Naka et al. |
| 5,250,554 A | 10/1993 | Naka et al. |
| 5,284,661 A | 2/1994 | Morimoto et al. |
| 5,328,919 A | 7/1994 | Naka et al. |
| 5,354,766 A | 10/1994 | Naka et al. |
| 5,389,641 A | 2/1995 | Naka et al. |
| 5,401,764 A | 3/1995 | Naka et al. |
| 5,463,073 A | 10/1995 | Takehiko et al. |
| 5,496,835 A | 3/1996 | Kubo et al. |
| 5,500,427 A | 3/1996 | Kubo et al. |
| 5,506,245 A | 4/1996 | Regnier et al. |
| 5,541,229 A | 7/1996 | Narr et al. |
| 5,565,469 A | 10/1996 | Mihm et al. |
| 5,583,141 A | 12/1996 | Naka et al. |
| 5,587,393 A | 12/1996 | Narr et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,639,773 A | 6/1997 | Kubo et al. |
| 5,663,186 A | 9/1997 | Nelson et al. |
| 5,663,187 A | 9/1997 | Nelson et al. |
| 5,684,029 A | 11/1997 | Narr et al. |
| 5,693,651 A | 12/1997 | Nomura et al. |
| 5,703,110 A | 12/1997 | Naka et al. |
| 5,705,517 A | 1/1998 | Naka et al. |
| 5,736,555 A | 4/1998 | Naka et al. |
| 5,741,803 A | 4/1998 | Pool et al. |
| 5,801,173 A | 9/1998 | Lohray et al. |
| 5,811,439 A | 9/1998 | Ogawa et al. |
| 5,817,075 A | 10/1998 | Giungo |
| 5,824,694 A | 10/1998 | Kurtz et al. |
| 5,827,865 A | 10/1998 | Haigh et al. |
| 5,834,501 A | 11/1998 | Fujita et al. |
| 5,843,172 A | 12/1998 | Yan |
| 5,843,970 A | 12/1998 | Pershadsingh et al. |
| 5,847,008 A | 12/1998 | Doebber et al. |
| 5,859,051 A | 1/1999 | Adams et al. |
| 5,864,043 A | 1/1999 | Narr et al. |
| 5,868,728 A | 2/1999 | Giungo et al. |
| 5,869,495 A | 2/1999 | Haigh et al. |
| 5,883,111 A | 3/1999 | Naka et al. |
| 5,885,997 A | 3/1999 | Lohray et al. |
| 5,886,014 A | 3/1999 | Fujita et al. |
| 5,889,025 A | 3/1999 | Lohray et al. |
| 5,889,032 A | 3/1999 | Lohray et al. |
| 5,902,726 A | 5/1999 | Kliewer et al. |
| 5,910,592 A | 6/1999 | Pool et al. |
| 5,919,782 A | 7/1999 | Lohray et al. |

(Continued)

FOREIGN PATENT DOCUMENTS

WO    WO 97/25042    7/1997

(Continued)

OTHER PUBLICATIONS

O'Donnell et al., "Irbesartan lowers blood pressure and ameliorates renal injury in experimental non-insulin-dependent diabetes mellitus", Kidney International, vol. 52, Suppl. 63, pp. S218-S200.*

(Continued)

*Primary Examiner*—Brian Kwon
(74) *Attorney, Agent, or Firm*—Morrison & Foerster LLP

(57) ABSTRACT

Methods are provided for treating or prophylactically preventing metabolic disorders in humans without causing, promoting, or aggravating fluid retention, peripheral edema, pulmonary edema, or congestive heart failure, by administration of a therapeutically effective amount of a compound sufficient to partially or fully activate peroxisome proliferator activated receptors (PPARs) and partially or fully inhibit, antagonize or block the activity of angiotensin II type 1 receptors. Metabolic disorders that can be treated or prevented include but are not limited to type 2 diabetes, the metabolic syndrome, prediabetes, and other insulin resistance syndromes. Compounds are provided that antagonize or block the angiotensin II type 1 (AT1) receptor, function as partial or full activators of peroxisome proliferator activated receptors (PPARs), can be used to treat or prevent diseases known to be treatable or preventable by PPAR activators and were not previously recognized to be therapeutic targets for angiotensin II receptor antagonists.

8 Claims, No Drawings

U.S. PATENT DOCUMENTS

| | | | |
|---|---|---|---|
| 5,925,656 A | 7/1999 | Kallam et al. | |
| 5,932,601 A | 8/1999 | Sohda et al. | |
| 5,939,442 A | 8/1999 | Evans et al. | |
| 5,952,356 A | 9/1999 | Ikeda et al. | |
| 5,952,509 A | 9/1999 | Saito et al. | |
| 5,958,942 A | 9/1999 | Takatani et al. | |
| 5,958,961 A | 9/1999 | Inada et al. | |
| 5,962,470 A | 10/1999 | Fujita et al. | |
| 5,962,491 A | 10/1999 | Naka et al. | |
| 5,965,584 A | 10/1999 | Ikeda et al. | |
| 5,968,589 A | 10/1999 | Murakami | |
| 5,972,959 A | 10/1999 | Yanagisawa et al. | |
| 5,972,970 A | 10/1999 | Sohda et al. | |
| 5,977,365 A | 11/1999 | Fujita et al. | |
| 5,985,884 A | 11/1999 | Lohray et al. | |
| 5,990,139 A | 11/1999 | Yano et al. | |
| 6,004,989 A | 12/1999 | Naka et al. | |
| 6,008,237 A | 12/1999 | Sahoo et al. | |
| 6,011,031 A | 1/2000 | Lohray et al. | |
| 6,011,036 A | 1/2000 | Lohray et al. | |
| RE36,575 E | 2/2000 | Meguro et al. | |
| 6,020,382 A | 2/2000 | Doebber et al. | |
| 6,022,897 A | 2/2000 | Evans et al. | |
| 6,028,088 A | 2/2000 | Pershadsingh et al. | |
| 6,087,384 A | 7/2000 | Matsui et al. | |
| 6,087,385 A | 7/2000 | Pershadsingh et al. | |
| 6,090,836 A | 7/2000 | Adams et al. | |
| 6,090,839 A | 7/2000 | Adams et al. | |
| 6,100,252 A * | 8/2000 | Naka et al. | 514/211.08 |
| 6,100,403 A | 8/2000 | Saito et al. | |
| 6,103,742 A | 8/2000 | Ikeda et al. | |
| 6,113,907 A | 9/2000 | Khwaja et al. | |
| 6,117,893 A | 9/2000 | Fujita et al. | |
| 6,150,371 A | 11/2000 | Fujiwara et al. | |
| 6,160,000 A | 12/2000 | Adams et al. | |
| 6,200,995 B1 | 3/2001 | De la Brouse-Elwood et al. | |
| 6,228,874 B1 | 5/2001 | Inada et al. | |
| 6,232,334 B1 | 5/2001 | Naka et al. | |
| 6,329,415 B1 | 12/2001 | Cirillo et al. | |
| 6,333,325 B1 | 12/2001 | Cirillo et al. | |
| 6,348,481 B2 | 2/2002 | Inada et al. | |
| 6,353,011 B1 | 3/2002 | Pershadsingh et al. | |
| 6,355,808 B2 | 3/2002 | Naka et al. | |
| 6,358,945 B1 | 3/2002 | Breitfelder et al. | |
| 6,369,098 B1 | 4/2002 | Pershadsingh et al. | |
| 6,372,773 B1 | 4/2002 | Regan | |
| 6,414,002 B1 | 7/2002 | Cheng et al. | |
| 6,414,008 B1 | 7/2002 | Hauel et al. | |
| 6,420,405 B2 | 7/2002 | Inada et al. | |
| 6,432,993 B1 | 8/2002 | Fujita et al. | |
| 6,432,996 B1 | 8/2002 | Tamura et al. | |
| 6,451,832 B2 | 9/2002 | Ries et al. | |
| 6,468,996 B1 | 10/2002 | Jeppesen et al. | |
| 6,469,039 B1 | 10/2002 | Hauel et al. | |
| 6,476,023 B1 | 11/2002 | Cirillo et al. | |
| 6,479,524 B1 | 11/2002 | Priepke et al. | |
| 6,486,188 B1 | 11/2002 | Pedersen et al. | |
| 2002/0048798 A1 | 4/2002 | Avery et al. | |

FOREIGN PATENT DOCUMENTS

| | | |
|---|---|---|
| WO | WO 97/28137 | 8/1997 |
| WO | WO 98/05331 | 2/1998 |
| WO | WO 98/57941 | 12/1998 |
| WO | WO 99/62870 | 12/1999 |
| WO | WO 99/62871 | 12/1999 |
| WO | WO 99/62872 | 12/1999 |
| WO | WO 00/27832 | 7/2000 |
| WO | WO 01/00603 | 1/2001 |
| WO | WO 01/12612 | 2/2001 |
| WO | WO 01/21602 | 3/2001 |
| WO | WO 01/34094 | 5/2001 |
| WO | WO-01/82858 A2 | 11/2001 |
| WO | WO-01/82858 A3 | 11/2001 |
| WO | WO 02/076177 | 10/2002 |

OTHER PUBLICATIONS

Beers et al., The Merck Manual of Medical Information, Second Edition, (2003), p. 922.*

GenBank Accession No. J03258, "Cloning and Expression of Full-Length cDNA Encoding Human Vitamin D Receptor" created on Jan. 14, 1995, located at <http://www.ncbi.nlm.nih.gov> last visited on Sep. 24, 2003.

GenBank Accession No. L02932, "cDNA Cloning, Chromosomal Mapping, and Functional Characterization of the Juman Peroxisome Proliferator Activated Receptor" created on Jul. 26, 1993, located at <http://www.ncbi.nlm.nih.gov> last visited on Sep. 24, 2003.

GenBank Accession No. L13740, "Isolation and Characterization of Human TR3 Receptor: A Member of Steroid Receptor Superfamily" created on Jun. 12, 1993, located at <http://www.ncbi.nlm.nih.gov> last visited on Sep. 24, 2003.

GenBank Accession No. L14160, "The Development of Sequence-Tagged Sites for Human Chromosome 4" created on Aug. 10, 1993, located at <http://www.ncbi.nlm.nih.gov> last visited on Sep. 24, 2003.

GenBank Accession No. L14611, "Identification of Nuclear Receptor mRNAs by RT-PCR Amplification of Conserved Zinc-Finger Motif Sequences" created on Oct. 16, 1993, located at <http://www.ncbi.nlm.nih.gov> last visited on Sep. 24, 2003.

GenBank Accession No. L27586, "Human and Rat TR4 Orphan Receptors Specify a Subclass of the Steroid Receptor Superfamily" created on Sep. 15, 1994, located at <http://www.ncbi.nlm.nih.gov> last visited on Sep. 24, 2003.

GenBank Accession No. L31785, "A New Orphan Member of the Nuclear Hormone Receptor Superfamily Closely Related to Rev-Erb" created on May 8, 1995, located at <http://www.ncbi.nlm.nih.gov> last visited on Sep. 24, 2003.

GenBank Accession No. L40904, "Isolation of the Human Peroxisome Proliferator Activated Receptor Gamma cDNA: Expression in Hematopoietic Cells and Chromosomal Mapping" created on Dec. 26, 2001, located at <http://www.ncbi.nlm.nih.gov> last visited on Sep. 24, 2003.

GenBank Accession No. M24748, "Characterization of a Third Human Thyroid Hormone Receptor Coexpressed with Other Thyroid Hormone Receptors in Several Tissues" created on May 9, 1995, located at <http://www.ncbi.nlm.nih.gov> last visited on Sep. 24, 2003.

GenBank Accession No. M24857, "A Third Human Retinoic Acid Receptor, hRAR-gamma" created on Nov. 8, 1994, located at <http://www.ncbi.nlm.nih.gov> last visited on Sep. 24, 2003.

GenBank Accession No. M24898, "Two erbA Homologs Encoding Proteins with Different T3 Binding Capacities are Transcribed from Opposite DNA Strands of the Same Genetic Locus" created on Nov. 7, 1994, located at <http://www.ncbi.nlm.nih.gov> last visited on Sep. 24, 2003.

GenBank Accession No. M26747, "Human Steroid Receptors and erbA Proto-Oncogene Products: Members of a New Superfamily of Enhancer Binding Proteins" created on Jun. 11, 2002, located at <http://www.ncbi.nlm.nih.gov> last visited on Sep. 24, 2003.

GenBank Accession No. M29960, "Molecular Cloning of New Human TR2 Receptors: A Class of Steroid Receptor with Multiple Ligand-Binding Domains" created on Aug. 3, 1993, located at <http://www.ncbi.nlm.nih.gov> last visited on Sep. 24, 2003.

GenBank Accession No. M64497, "Regulation of the Apolipoprotein AI Gene by ARP-1, a Novel Member of the Steroid Receptor Superfamily" created on Jan. 31, 1996, located at <http://www.ncbi.nlm.nih.gov> last visited on Sep. 24, 2003.

GenBank Accession No. M81385, "Expression and Functional Analysisi of Liver Receptor Homologue-1 as a Potential Steroidogenic Factor in Rat Ovary" created on Jul. 22, 2003, located at <http://www.ncbi.nlm.nih.gov> last visited on Sep. 24, 2003.

GenBank Accession No. M84820, "Purification, Cloning, and RXR Identity of the HeLa Cell Factor with which RAR or TR Heterodimerizes to Bind Target Sequences Efficiently" created on Jan. 9, 1995, located at <http://www.ncbi.nlm.nih.gov> last visited on Sep. 24, 2003.
GenBank Accession No. S65876, "Characterization of the Mouse FTZ-F1 Gene, which Encodes a Key Regulator of Steroid Hydroxylase Gene Expression" created on May 8, 2002, located at <http://www.ncbi.nlm.nih.gov> last visited on Sep. 24, 2003.
GenBank Accession No. S77482, "The Mouse Homolog of the Orphan Nuclear Receptor Tailless is Expressed in the Developing Forebrain" created on Sep. 27, 1995, located at <http://www.ncbi.nlm.nih.gov> last visited on Sep. 24, 2003.
GenBank Accession No. U10375, "Differential Expression and Activation of a Family of Murine Peroxisome Proliferator-Activated Receptors" created on Jul. 22, 1994, located at <http://www.ncbi.nlm.nih.gov> last visited on Sep. 24, 2003.
GenBank Accession No. U11551, "A Novel Bacillus Associated with Diseased Fish" created on Jul. 19, 1994, located at <http://www.ncbi.nlm.nih.gov> last visited on Sep. 24, 2003.
GenBank Accession No. U12767, "The Isolation and Characterization of MINOR, a Novel Mitogen-Inducible Nuclear Orphan Receptor" created on Jun. 17, 1996, located at <http://www.ncbi.nlm.nih.gov> last visited on Sep. 24, 2003.
GenBank Accession No. U14534, "Ubiquitous Receptor: A Novel Receptor That Modulates Gene Activation by Retinoic Acid and Thyroid Hormone Receptors" created on Jan. 2, 1995, located at <http://www.ncbi.nlm.nih.gov> last visited on Sep. 24, 2003.
GenBank Accession No. U14666, "Cloning of a Novel Orphan Receptor (GCNF) Expressed During Germ Cell Development" created on Mar. 23, 1996, located at <http://www.ncbi.nlm.nih.gov> last visited on Sep. 24, 2003.
GenBank Accession No. U16997, "ROR Gamma: The Third Member of ROR/RZR Orphan Receptor Subfamily that is Highly Expressed in Skeletal Muscle" created on Apr. 4, 1995, located at <http://www.ncbi.nlm.nih.gov> last visited on Sep. 24, 2003.
GenBank Accession No. U18374, "Identification of a Nuclear Receptor that is Activated by Farnesol Metabolites" created on Jun. 21, 1995, located at <http://www.ncbi.nlm.nih.gov> last visited on Sep. 24, 2003.
GenBank Accession No. U38480, "Characterization of Three RXR Genes that Mediate the Action of 9-cis Retinoic Acid" created on Nov. 8, 1995, located at <http://www.ncbi.nlm.nih.gov> last visited on Sep. 24, 2003.
GenBank Accession No. X06614, "A Transferable Silencing Domain is Present in the Thyroid Hormone Receptor, in the v-erbA Oncogene Product and in the Retinoic Acid Receptor" created on Sep. 12, 1993, located at <http://www.ncbi.nlm.nih.gov> last visited on Sep. 24, 2003.
GenBank Accession No. X12794, "Identification of Two Novel Members of erbA Superfamily by Molecular Cloning: The Gene Products of the Two are Highly Related to Each Other" created on Jun. 25, 1997, located at <http://www.ncbi.nlm.nih.gov> last visited on Sep. 24, 2003.
GenBank Accession No. X12795, "Identification of Two Novel Members of erbA Superfamily by Molecular Cloning: The Gene Products of the Two are Highly Related to Each Other" created on Jun. 25, 1997, located at <http://www.ncbi.nlm.nih.gov> last visited on Sep. 24, 2003.
GenBank Accession No. X51416, "Identification of a New Class of Steroid Hormone Receptors" created on Apr. 3, 1997, located at <http://www.ncbi.nlm.nih.gov> last visited on Sep. 24, 2003.
GenBank Accession No. X51417, "Identification of a New Class of Steroid Hormone Receptors" created on Feb. 10, 1999, located at <http://www.ncbi.nlm.nih.gov> last visited on Sep. 24, 2003.
GenBank Accession No. X52773, "Nuclear Receptor That Identifies a Novel Retinoic Acid Response Pathway" created on Sep. 12, 1993, located at <http://www.ncbi.nlm.nih.gov> last visited on Sep. 24, 2003.
GenBank Accession No. X75163 "A Novel Nuclear Receptor Superfamily Member in Xenopus That Associates with RXR, and Shares Extensive Sequence Similiarity to the Mammalian Vitamin D3 Receptor" created on Feb. 2, 1994, located at <http://www.ncbi.nlm.nih.gov> last visited on Sep. 24, 2003.

GenBank Accession No. X75918, "NOT, a Human Immediate-Early Response Gene Closely Related to the Steroid/Thyroid Hormone Receptor NAK1/TR3" created on Jan. 6, 1995, located at <http://www.ncbi.nlm.nih.gov> last visited on Sep. 24, 2003.
GenBank Accession No. X76930, "Clonign and Sequencing of cDNAs Encoding the Human Hepatocyte Nuclear Factor 4 Indicate the Presence of Two Isoforms in Human Liver" created on Nov. 8, 1994, located at <http://www.ncbi.nlm.nih.gov> last visited on Sep. 24, 2003.
GenBank Accession No. Y00291, "A Novel Steroid Thyroid Hormone Receptor-Related Gene Inappropiately Expressed in Human Hepatocellular Carcinoma" created on Jan. 14, 1991, located at <http://www.ncbi.nlm.nih.gov> last visited on Sep. 24, 2003.
GenBank Accession No. Z49826, "Human Hepatocyte Nuclear Factor 4 Isoforms Are Encoded by Distinct and Differentially Expressed Genes" created on Sep. 6, 1999, located at <http://www.ncbi.nlm.nih.gov> last visited on Sep. 24, 2003.
Adams, A.D. et al. (2003). "Amphipathic 3-Phenyl-7-propylbenzisoxazoles; Human PPaR $\gamma$, $\delta$ and $\alpha$ Agonists," *Bioorganic & Medicinal Chemistry Letters* 13:931-935.
Alberti, K.G.M.M. and Zimmet, P.Z. (1998). "Definition, Diagnoisis and Classification of Diabetes Mellitus and its Complications. Part 1: Diagnosis and Classification of Diabetes Mellitus Provisional Report of a WHO Consultation," *Diabet. Med.* 15:539-553.
Almansa, C. et al., (1996). "Diphenylpropionic Acids as New $AT_1$ Selective Angiotensin II Antagonists," *J. Med. Chem.* 39:2197-2206.
Almansa, C. et al. (1997). "Synthesis and Structure-Activity Relationship of a New Series of Potent $AT_1$ Selective Angiotensin II Receptor Antagonists: 5-(Biphenyl-4-ylmethyl)pyrazoles," *J. Med. Chem.* 40:547-558.
American Diabetes Association (2002). "The Prevention or Delay of Type 2 Diabetes," *Diabetes Care* 25(4)742-749.
American Medical Association. (2001). "Executive Summary of the Third Report of the National Cholesterol Education Program (NCEP) Expert Panel on Detection, Evaluation, and Treatment of High Blood Cholesterol in Adults (Adult Treatment Panel III)," *JAMA*, 285(19):2486-2497.
American Medical Association. (2002). "Major Outcomes in High-Risk Hypertensive Patients Randomized to Angiotensin-Converting Enzyme Inhibitor or Calcium Channel Blocker vs Diuretic: The Antihypertensive and Lipid-Lowering Treatment to Prevent Heart Attack Trial (ALLHAT)," *JAMA* 288(23):2981-2997.
Ashton, W.T. et al. (1994). "Triazolinone Biphenylsulfonamide Derivatives as Orally Active Angiotensin II Antagonists with Potent $AT_1$ Receptor Affinity and Enhanced $AT_2$ Affinity," *J. Med. Chem.* 37:2808-2824.
Atwal, K.S. et al. (1992). "Dihydropyrimidine Angiotensin II Receptor Antagonists," *J. Med. Chem.* 35:4751-4763.
Bernhart, C.A. et al. (1993). "A New Series of Imidazolones: Highly Specific and Potent Nonpeptide $AT_1$ Angiotensin II Receptor Antagonists," *J. Med. Chem.* 36:3371-3380.
Bernobich, E. et al. (2002). "The Role of the Angiotensin System in Cardiac Glucose Homeostasis: Therapeutic Implications," *Drugs* 62(9):1295-1314.
Blankley, C.J. et al. (1991). "Synthesis and Structure-Activity Relationships of a Novel Series of Non-Peptide Angiotensin II Receptor Binding Inhibitors Specific for the $AT_2$ Subtype," *J. Med. Chem.* 34:3248-3260.
Brasier, A.R. et al. (2000). "Angiotensin II Induces Gene Transcription Through Cell-Type-Dependent Effects on the Nuclear Factor-κB (NF-κB) Transcription Factor," *Mol. Cell. Biochem.* 212:155-169.
Brooks, D.A. et al. (2001). "Design and Synthesis of 2-Methyl-2-{4-[2-(5-methyl-2-aryloxazol-4-yl)ethoxy]phenoxy}propionic Acids: A New Class of Dual PPARα/γ Agonists," *J. Med. Chem.* 44:2061-2064.
Bühlmayer, P. et al. (1991). "Nonpeptidic Angiotensin II Antagonists: Synthesis and in Vitro Activity of a Series of Novel Naphthalene and Tetrahydronaphthalene Derivatives," *J. Med. Chem.* 34:3105-3114.

Carini, D.J. et al. (1991). "Nonpeptide Angiotensin II Receptor Antagonists: The Discovery of a Series of N-(Biphenylylmethyl)Imidazoles as Potent, Orally Active Antihypertensives," *J. Med. Chem.* 34:2525-2547.

Cronet, P. et al. (2001). "Structure of the PPARα and -γ Ligand Binding Domain in Complex with AZ 242; Ligand Selectivity and Agonist Activation in the PPAR Family," *Structure* 9:699-706.

Dahlöf, B. et al. (2002). "Cardiovascular Morbidity and Mortality in the Losartan Intervention For Endpoint Reduction in Hypertension Study (LIFE): A Randomised Trial Against Atenolol," *The Lancet* 359:995-1003.

Danforth, E. Jr. (2000). "Failure of Adipocyte Differentiation Causes Type II Diabetes Mellitus?" *Nat. Genet.* 26:13.

De, B. et al. (1992). "Discovery of a Novel Class of Orally Active, Non-Peptide Angiotensin II Antagonists," *J. Med. Chem.* 35:3714-3717.

Dhanoa, D.S. et al. (1993). "(Dipropylphenoxy)phenylacetic Acids: A New Generation of Nonpeptide Angiotensin II Receptor Antagonists," *J. Med. Chem.* 36:3738-3742.

Easthope, S.E. and Jarvis, B. (2002). "Candesartan Cilexetil: An Update of its Use in Essential Hypertension," *Drugs* 62(8):1253-1287.

Ellingboe, J.W. et al. (1998). "Metabolites of the Angiotensin II Antagonist Tasosartan: The Importance of a Second Acidic Group," *J. Med. Chem.* 41:4251-4260.

Epstein, M. (2002). "Angiotensin II Receptor Antagonists: Current Status" Chapter 17 *In Angiotensin II Receptor Antagonists* Epstein, M. and Brunner, H.R. eds. Hanley and Belfus, Inc.: Philadelphia, PA. pp. 257-261.

Ford, E.S. et al. (2002). "Prevalence of the Metabolic Syndrome Among US Adults: Findings From the Third National Health and Nutrition Examination Survey," *JAMA* 287(3):356-359.

Galvin, P. et al. (1992). "A Simple Method for Quantitation of Insulin Sensitivity and Insulin Release From an Intravenous Glucose Tolerance Test," *Diabetic Medicine* 9:921-928.

Groff, J.L. et al. (1993). "Simplified Enzymatic Assay of Angiotensin-Converting Enzyme in Serum," *Clin. Chem.* 39(3):400-404.

Hansson, L. et al. (1999). "Effect of Angiotensin-Converting-Enzyme Inhibition Compared with Conventional Therapy on Cardiovascular Morbidity and Mortality in Hypertension: The Captopril Prevention Project (CAPPP) Randomised Trial," *The Lancet* 353:611-616.

Henke, B.R. et al. (1998). "N-(2-Benzoylphenyl)-L-Tyrosine PPARγ Agonists. 1. Discovery of a Novel Series of Potent Antihyperglycemic and Antihyperlipidemic Agents," *J. Med. Chem.* 41:5020-5036.

Henriksen, E.J. et al. (2001). "Selective Angiotensin II Receptor Antagonism Reduces Insulin Resistance in Obese Zucker Rats," *Hypertension* 38:884-890.

Horiuchi, M. et al. (2003). "Fluvastatin Enhances the Inhibitory Effects of a Selective Angiotensin II Type 1 Receptor Blocker, Valsartan, on Vascular Neointimal Formation," *Circulation* 107:106-112.

Janke, J. et al. (2002). "Mature Adipocytes Inhibit In Vitro Differentiation of Human Preadipocytes Via Angiotensin Type 1 Receptors," *Diabetes* 51:1699-1707.

Katsuki, A. et al. (2001). "Homeostasis Model Assessment Is a Reliable Indicator of Insulin Resistance During Follow-up of Patients With Type 2 Diabetes," *Diabetes Care* 24(2):362-365.

Kubo, K. et al. (1993). "Nonpeptide Angiotensin II Receptor Antagonists. Synthesis and Biological Activity of Benzimidazoles," *J. Med. Chem.* 36:1772-1784.

Laaksonen, D.E. et al. (2002). "Metabolic Syndrome and Development of Diabetes Mellitus: Application and Validation of Recently Suggested Definitions of the Metabolic Syndrome in a Prospective Cohort Study," *American Journal of Epidemiology* 156(11):1070-1077.

Le Bourdonnec, B. et al. (2000). "Synthesis and Pharmacological Evaluation of New Pyrazolidine-3, 5-diones as $AT_1$ Receptor Antagonists," *J. Med. Chem.* 43:2685-2697.

Le Bourdonnec, B. et al. (2002). "Comparison of 3D Structures and $AT_1$ Binding Properties of Pyrazolidine-3,5-diones and Tetrahydropyridazine-3,6-diones with Parent Antihypertensive Drug Irbesartan," *J. Med. Chem.* 45:4794-4798.

Lin, H.S. et al. (1992). "Nonpeptide Angiotensin II Receptor Antagonists: Synthetic and Computational Chemistry of N-[[4-(2H-Tetrazol-5-yl)-1-Cycloalken-1-yl]Phenyl]Methyl]Imidazole Derivatives and Their In Vitro Activity," *J. Med. Chem.* 35:2658-2667.

Maillard, M.P. et al. (2002). "Pharmacodynamics and Drug Action: Comparative Angiotensin II Receptor Blockade in Healthy Volunteers: The Importance of Dosing," *Clin. Pharmacol. Ther.* 71(1):1632-1645.

Mederski, W.W.K.R. et al. (1994). "Non-Peptide Angiotensin II Receptor Antagonists: Synthesis and Biological Activity of a Series of Novel 4,5-Dihydro-4-oxo-3H-imidazo(4,5-c)pyridine Derivatives," *J. Med. Chem.* 37:1632-1645.

Meigs, J.B. et al. (2003). "The Natural History of Progression From Normal Glucose Tolerance to Type 2 Diabetes in the Baltimore Longitudinal Study of Aging," *Diabetes* 52:1475-1484.

Miyajima, A. et al. (2002). "Angiotensin II Type I Antagonist Prevents Pulmonary Metastasis of Murine Renal Cancer by Inhibiting Tumor Angiogensis," *Cancer Res.* 62:4176-4179.

Miyazaki, M. et al. (1999). "Angiotensin II Type I Receptor Antagonist, TCV-116, Prevents Neointima Formation in Injured Arteries in the Dog," *Jpn. J. Pharmacol.* 79:455-460.

Nelson, K.A. et al. (1994). "The Cancer Anorexia-Cachexia Syndrome," *Journal of Clinical Oncology* 12(1):213-225.

Norman, M.H. et al. (1995). "4-(Heteroarylthio)-2-biphenylyltetrazoles as Nonpeptide Angiotensin II Antagonists," *J. Med. Chem.* 38:4670-4778.

Phillips, M.I. and Kagiyama, S. (2002). "Angiotensin II As A Pro-Inflammatory Mediator," *Curr. Opin. Investig. Drugs* 3(4):569-577.

Sasaki, K. et al. (2002). "Evidence for the Importance of Angiotensin II Type I Receptor in Ischemia-Induced Angiogenesis," *J. Clin. Invest.* 109:603-611.

Schmidt, B. and Schieffer, B. (2003). "Angiotensin II AT1 Receptor Antagonists. Clinical Implications of Active Metabolites," *J. Med. Chem.* 46(12):2261-2270.

Sharma, A.M. et al. (2002). "Angiotensin Blockade Prevents Type 2 Diabetes by Formation of Fat Cells," *Hypertension* 40:609-611.

Shiuchi, T. et al. (2002). "ACE Inhibitor Improves Insulin Resistance in Diabetic Mouse via Bradykinin and NO," *Hypertension* 40:329-334.

Silvestre, J.S. et al. (2002). "Antiangiogenic Effect of Angiotensin II Type 2 Receptor in Ischemia-Induced Angiogenesis in Mice Hindlimb," *Circ. Res.* 90:1072-1079.

Smith, K.L. and Tisdale, M.J. (1993). "Mechanism of Muscle Protein Degradation in Cancer Cachexia," *British Journal of Cancer* 68:314-318.

Tamarat, R. et al. (2002). "Angiotensin II Angiogenic Effect in Vivo Involves Vascular Endothelial Growth Factor- and Inflammation-Related Pathways," *Lab. Invest.* 82(6):747-756.

Tanaka, Y. et al. (1989). "Antitumor Activity of Indomethacin in Mice Bearing Advanced Colon 26 Carcinoma Compared with Those with Early Transplants," *Cancer Research* 49:5935-5939.

Teuscher, A.U. and Weidmann, P.U. (1997). "Requirements for Antihypertensive Therapy in Diabetic Patients: Metabolic Aspects," *Journal of Hypertension* 15(Supp. 2):S67-S75.

Tham, D.M. et al. (2002). "Angiotensin II Is Associated With Activation of NF-κB-Mediated Genes and Downregulation of PPARs," *Physiol. Genomics* 11:21-30.

Tomiyama, H. et al. (1994). "Kinins Contribute to the Improvement of Insulin Sensitivity During Treatment with Angiotensin Converting Enzyme Inhibitor," *Hypertension* 23:450-455.

Wang, N. et al. (2002). "Constitutive Activation of Peroxisome Proliferator-Activated Receptor-γ Suppresses Pro-Inflammatory Adhesion Molecules in Human Vascular Endothelial Cells," *J. Biol. Chem.* 277(37):34176-34181.

Yusuf, S. et al. (2001). "Ramipril and the Development of Diabetes," *JAMA* 286:1882-1885.

Zimmet, P. et al. (2001). "Global and Societal Implications of the Diabetes Epidemic," *Nature* 414:782-787.

Database Medline on STN (Columbus, OH, USA) Document No. 22006210, Accession No. 2002271257. Diep, Q. et al. (2002). "Structure, Edothelial Function, Cell Growth, and Inflammation in Blood Vessels of Angiotensin II- Infused Rats: Role Peroxisome Proliferator-Activated Receptor-Gamma," *Circulation* 105(9):2296-2302, abstract, 3 pages.

Database HCAPLUS on STN (Columbus, OH, USA) Document No. 133:41183, Accession No. 2000:195273. Vamecq, J. et al. (2000). "Peroxisome Proliferator-Activated Receptors (PPARs) and Their Implications in Diseases," *Current Opinion in Endocrinology & Diabetes* 7(1):8-18, abstract, 1 page.

International Search Report mailed on Jun. 18, 2004, for PCT patent application No. PCT/US03/24881 filed on Aug. 8, 2003, 5 pages.

Asmar, R. et al. (Apr. 2001). "Effects of Telmisartan on Arterial Compliance and Endothelial Function in Type 2 Diabetes Patients with Essential Hypertension," *American Journal of Hypertension* 14(4):114A, Abstract P-254, one page.

Supplementary Partial European Search Report mailed Sep. 29, 2005, for EP Patent Application No. 03785060.9, filed Aug. 8, 2003, five pages.

Wienen, W. et al. (Mar. 2001). "Comparative Antihypertensive and Renoprotective Effects of Telmisartan and Lisinopril After Long-Term Treatment in Hypertensive Diabetic Rats," *J. of the Renin-Angiotensin- Aldosterone System* 2(1):31-36.

\* cited by examiner

PPAR LIGANDS THAT DO NOT CAUSE FLUID RETENTION, EDEMA OR CONGESTIVE HEART FAILURE

CROSS-REFERENCE TO RELATED APPLICATIONS

This application claims benefit under 35 U.S.C. §119(e) of provisional application U.S. Ser. No. 60/402,425, filed on Aug. 10, 2002, and provisional application U.S. Ser. No. 60/455,211 filed on Mar. 15, 2003, which are herein incorporated by reference in their entirety for all purposes.

TECHNICAL FIELD OF THE INVENTION

This invention relates to the field of prevention and treatment of cardiovascular diseases and insulin resistance syndromes. Specifically, this invention relates to compounds that increase both the activity of peroxisome proliferator activated receptors (PPARs) and blocks/antagonizes activity of the angiotensin II type 1 receptor. More specifically, this invention relates to novel clinical uses of certain angiotensin II type 1 receptor blockers (ARBs) which can increase the activity of peroxisome proliferator activated receptors (PPARs).

BACKGROUND OF THE INVENTION

Peroxisome proliferator-activated receptors (PPARs) are members of the nuclear receptor superfamily of ligand-activated transcription factors. Three subtypes of PPARs have been cloned from the mouse and human: i.e., PPARα, PPARγ, and PPARδ. The PPARs are important regulators of carbohydrate and lipid metabolism, cell growth and differentiation, phenotype transition, apoptosis, neovascularization, immunoregulation and the inflammatory response. Compounds that activate PPARs are useful for the treatment and prevention of a variety of clinical disorders including but not limited to the metabolic syndrome, obesity, pre-diabetes, type 2 diabetes, and other insulin resistant syndromes, hypertension, atherosclerosis, dyslipidemia, inflammatory skin diseases such as psoriasis, inflammatory bowel disease, and inflammatory neurodegenerative diseases such as multiple sclerosis and Alzheimer's disease. The metabolic syndrome as referred to herein includes the metabolic syndrome as defined by either the World Health Organization (WHO) or the National Cholesterol Education Program (NCEP) (Zimmet P, et al. *Global and societal implications of the diabetes epidemic*. Nature. (2001) 414:782-7; Alberti K G, Zimmet P Z. *Definition, diagnosis and classification of diabetes mellitus and its complications. Part 1: diagnosis and classification of diabetes mellitus provisional report of a WHO consultation*. Diabet Med. (1998) 15:539-53; *Executive Summary of The Third Report of The National Cholesterol Education Program (NCEP) Expert Panel on Detection, Evaluation, And Treatment of High Blood Cholesterol In Adults (Adult Treatment Panel III)*. JAMA (2001) 285: 2486-97.).

Examples of known compounds that can activate PPARs include thiazolidinediones (e.g. rosiglitazone, pioglitazone, MK 767 (KRP-297), MCC-555, netoglitazone, balaglitazone, rivoglitazone) that primarily activate PPARgamma or PPARgamma and PPARalpha, and non-thiazolidinediones that can activate any combination of PPARgamma, PPARalpha and PPARdelta (e,g, JTT-501, LSN862, DRF 4832, LM 4156, LY 510929, LY 519818, TY 51501, X 334), certain tyrosine-based derivatives (e.g. GW1929, GW7845), phenylacetic acid-based derivatives, phenoxazine phenyl propanoic acid derivatives (e.g. DRF 2725, DRF 2189), cinammic and dihydrocinammic acid-based derivatives (e.g. tesaglitazar (AZ 242)), and 3-Phenyl-7-propylbenzisoxazoles (Adams A D, et al. Bioorg Med Chem Lett. (2003) 13:931-5), that can activate PPARgamma in combination with PPARalpha or PPARdelta or both PPARalpha and PPARdelta. Although compounds are available that may primarily activate PPARalpha alone or PPARdelta alone, it is common for such compounds to also cause at least some degree of PPARgamma activation as well.

Although drugs that activate PPARgamma have proven to be valuable for the prevention and treatment of type 2 diabetes and a variety of other disorders, the currently available agents cause adverse effects or aggravate certain conditions that can limit the clinical utility and safety of these ligands. Some of the principle limiting side effects or conditions that can be provoked or aggravated by both thiazolidinedione and non-thiazolidinedione compounds that activate PPARgamma either alone or in combination with other PPARs are fluid retention, peripheral edema, pulmonary edema, and congestive heart failure. Both rosiglitazone and pioglitazone have received regulatory approval for the treatment of type 2 diabetes in many countries including the United States and throughout the European Community. The extensive accumulated experience with worldwide use of these drugs has revealed that thiazolidinediones can cause fluid retention, which exacerbates or leads to edema and/or congestive heart failure (CHF). Patients with ongoing edema are prone to adverse effects when on thiazolidinedione therapy, and especially if this is combined with administration with insulin, consisting of up to 16% of patients in the latter group. This is potentially a serious problem, considering that among patients with type 2 diabetes likely to be treated with thiazolidinediones or other non-thiazolidinedione agonist, a significant percentage have CHF or are at high risk for developing CHF because of their high cardiovascular risk profiles. Fluid retention caused by PPAR activators can not only cause volume expansion and peripheral edema, but also can also induce or aggravate life-threatening conditions such as CHF and pulmonary edema. Therefore, there is considerable interest in identifying and using PPARgamma activators that do not cause substantial fluid retention and therefore do not increase the risk for edema and congestive heart failure.

The current invention relates to the surprising discovery that certain ARBs can increase the activity of PPARgamma and can be used to treat or prevent type 2 diabetes, the metabolic syndrome, and other disorders responsive to PPAR activators or PPAR activation, without increasing the risk for fluid retention, peripheral edema, pulmonary edema, or congestive heart failure. Although previous studies have shown that the risk for type 2 diabetes in patients given ARBs is lower than that in patients given other antihypertensive drugs, it could not have been predicted that certain ARBs could be used to prevent or treat type 2 diabetes, the metabolic syndrome or other disorders responsive to PPAR ligands.

It has been unclear whether ARBs actually decreased the risk for diabetes or whether the drugs to which they were being compared increased the risk for diabetes. For example, the lower risk of diabetes reported in patients given ARBs versus beta blockers or thiazide diuretics was due to the fact that beta blockers and thiazide diuretics aggravate insulin resistance and therefore, the results of clinical studies comparing ARBs to other agents cannot be used to predict whether ARBs can be used to prevent or treat diabetes or other disorders responsive to PPARgamma activators.

Several trials have investigated the effects of ARBs on glucose homeostasis but the results are conflicting and controversial (for a review of this subject, see: Bernobich E, et al. Drugs (2002) 62:1295-1314). There are no data available that consistently demonstrate that ARBs improve insulin sensitivity, attenuate insulin resistance, or can be used to treat or prevent type 2 diabetes, the metabolic syndrome, or other insulin resistance syndromes. Expert opinions expressed in the medical and scientific literature hold that drugs that block angiotensin II type 1 receptors (ARBs) (also known as "sartans") are "metabolically neutral" (Epstein M. *Angiotensin II Receptor Antagonists: Current Status. In: Angiotensin II Receptor Antagonists*. Epstein M and Brunner H R (eds), Hanley & Belfus, Inc., Philadelphia, (2002) pp 257-261). For example, the ARB losartan has a neutral effect on glucose metabolism, insulin sensitivity, and serum concentrations in patients with mild hypertension (Bernobich E, et al. Drugs (2002) 62:1295-1314), and in clinical studies with diabetic patients, candesartan does not appreciably alter their hemoglobin A1c, glucose concentration or lipid profile (Easthope S E, et al. Drugs 2002;62:1253-87).

In a recent clinical trial (LIFE trial) where the ARB losartan was compared to the β-blocker atenolol, the incidence of new-onset type 2 diabetes was greater in the atenolol treated patients than in those treated with losartan (Dahlof B, et al. Lancet (2002) 359:995-1003). However, β-blockers like atenolol are known to be clinically diabetogenic and can promote or worsen insulin resistance and thereby promote the development of type 2 diabetes (Teuscher A U, et al. J Hypertens Suppl. (1997) 15:S67-75). Therefore, the lower incidence of new-onset type 2 diabetes in the losartan arm of the study actually reflected an increase in the incidence of new-onset type 2 diabetes in the atenolol arm. Studies showing a lower incidence of new onset diabetes in patients treated with the ARB candesartan compared to patients treated with thiazide diuretics also indicate that the ARB candesartan did not decrease the risk for diabetes, rather, the thiazide diuretic increased the risk for diabetes. Consequently, the prior art could not be used to predict that losartan, telmisartan, irbesartan, or any other ARB could be used to prevent or treat type 2 diabetes, the metabolic syndrome, or other forms of insulin resistance. Moreover, because the ARBs have important structural chemical differences, any unusual or unexpected results obtained with one ARB cannot be used to predict that similar results would be obtained with another ARB.

In the obese Zucker rat, Henriksen et al. found that oral administration of an extremely high dose of irbesartan improved insulin sensitivity but apparently failed to improve lipid levels (Henriksen E J, et al. *Selective angiotensin II receptor antagonism reduces insulin resistance in obese Zucker rats*. Hypertension. (2001) 38:884-90). However, the obese Zucker rat is an unusual form of obesity and insulin resistance that is caused by mutations in the leptin receptor and furthermore, the rats studied by Henriksen did not have type 2 diabetes. Mutations in leptin receptors in humans are extremely rare and almost never account for type 2 diabetes, obesity, insulin resistance, or the metabolic syndrome in humans. Therefore, the studies by Henriksen et al. in which an extremely high dose of irbesartan was found to improve insulin sensitivity in obese Zucker rats can not be used to predict or imply that irbesartan or any other ARB could be used to activate PPARγ in vivo or be used to treat or prevent type 2 diabetes, the metabolic syndrome, or other insulin resistance syndromes in humans.

In 2002, after the current discovery was made, Sharma and colleagues reported that very high concentrations of angiotensin II can inhibit differentiation of human preadipocytes and that high concentrations of irbesartan can enhance adipogenesis (Janke J, et al. *Mature adipocytes inhibit in vitro differentiation of human preadipocytes via angiotensin type 1 receptors*. Diabetes. (2002) 51:1699-707). Based on these findings and recent evidence showing that lack of adipose tissue can promote diabetes by causing excess storage of fat in muscle, liver, and pancreas (Danforth E, Jr. *Failure of adipocyte differentiation causes type II diabetes mellitus?* Nat Genet. (2000) 26:13), Sharma and colleagues proposed that blockade of the renin-angiotensin system per se might prevent diabetes by promoting the recruitment and differentiation of adipocytes (Sharma A M, et al. *Angiotensin blockade prevents type 2 diabetes by formation of fat cells*. Hypertension. (2002) 40:609-11). In the current studies, we have found that moderate concentrations of telmisartan and higher concentrations of irbesartan can activate PPARγ which is known to promote adipogenesis, however, other ARBs failed to show any effects on PPARγ gamma activity or adipogenesis. Thus, blockade of angiotensin receptors per se is not sufficient to promote increased PPARgamma activity or adipogenesis and not sufficient to prevent or treat type 2 diabetes or any other insulin resistance syndrome including the metabolic syndrome.

In light of a number of clinical and experimental studies suggesting that angiotensin converting enzyme (ACE) inhibitors can improve insulin sensitivity and decrease the incidence of new onset type 2 diabetes in patients with hypertension, the question again arises as to whether pharmacological interruption of the renin-angiotensin system by other means, such as with angiotensin receptor blockers (ARBs), could also be predicted to be useful for preventing or treating type 2 diabetes or other insulin resistance syndromes (Yusuf S, et al. *Ramipril and the development of diabetes*. JAMA. 2001;286:1882-5; Hansson L, et al. *Effect of angiotensin-converting-enzyme inhibition compared with conventional therapy on cardiovascular morbidity and mortality in hypertension: the Captopril Prevention Project (CAPPP) randomized trial*. Lancet. (1999) 353:611-6; *Major outcomes in high-risk hypertensive patients randomized to angiotensin-converting enzyme inhibitor or calcium channel blocker vs diuretic: The Antihypertensive and Lipid-Lowering Treatment to Prevent Heart Attack Trial (ALLHAT)*. JAMA. (2002) 288:2981-97; Bernobich E, et al. *The role of the angiotensin system in cardiac glucose homeostasis: therapeutic implications*. Drugs. (2002) 62:1295-314). However, recent studies have shown that the insulin sensitizing effects of ACE inhibitors are related to their effects on kinin metabolism rather than their effects on the renin-angiotensin system (Tomiyama H, et al. Kinins contribute to the improvement of insulin sensitivity during treatment with angiotensin converting enzyme inhibitor. Hypertension. (1994) 23:450-5; Shiuchi T, et al. ACE inhibitor improves insulin resistance in diabetic mouse via bradykinin and NO. Hypertension. (2002) 40:329-34; Bernobich E, et al. The role of the angiotensin system in cardiac glucose homeostasis: therapeutic implications. Drugs. (2002) 62:1295-314). Thus, based on the results of studies using ACE inhibitors, it could not have been predicted that any of the existing ARBs would activate PPARγ and be useful for preventing or treating type 2 diabetes, the metabolic syndrome or any other insulin resistance syndrome.

SUMMARY OF THE INVENTION

While not wishing to be bound by theory, drugs that activate PPARgamma can cause fluid retention through a number of mechanisms. A surprising feature of this invention is that the fluid retention usually caused by drugs that activate PPARgamma can be prevented or attenuated by blockade of angiotensin II type 1 receptors. Because multiple mechanisms may be involved in the fluid retention caused by PPARgamma ligands, it could not have been predicted that blockade of angiotensin receptors could prevent or attenuate the fluid retention caused by PPARgamma ligands in humans. Thus, it could not have been predicted that ARBs that activate PPAR could be used to treat or prevent type 2 diabetes, the metabolic syndrome, or other insulin resistance syndromes without increasing the risk for fluid retention, edema, or congestive heart failure.

Until the current discovery described herein, it was not known that certain ARBs could increase the activity of PPARgamma. Thus, it could also not have been predicted that certain ARBs could be used to treat or prevent insulin resistance syndromes, type 2 diabetes, the metabolic syndrome or other conditions known to be treatable by drugs that increase the activity of PPARgamma.

The current discovery also provides improved methods for preventing and treating inflammatory diseases without promoting or aggravating fluid retention, peripheral edema, pulmonary edema, or congestive heart failure by administering PPAR activators that also antagonize the angiotensin II type 1 receptor. Although it has long been recognized that compounds that activate PPAR or block angiotensin II type 1 receptors have anti-inflammatory effects, it could not have been predicted that certain compounds would have the capacity to both activate PPARs and block angiotensin receptors. Because such compounds exert anti-inflammatory effects through multiple pathways (PPAR pathway and the angiotensin receptor pathway), they provide a superior ability to treat or prevent inflammatory diseases than PPAR activators or ARBs alone. Such compounds that activate PPARs and block angiotensin receptors are also superior to PPAR activators because unlike currently recognized PPAR activators, the compounds of the current invention do not promote or aggravate fluid retention, peripheral edema, pulmonary edema or heart failure.

The current invention describes the surprising finding that drugs exist and can be developed that block the angiotensin II Type 1 receptor (angiotensin receptor blockers or ARBs) and can also increase the activity of PPARgamma. That is, some drugs exist that can function as both an ARB and as a PPAR activator. Such agents include, but are not limited to, telmisartan and irbesartan and can be used to prevent or treat type 2 diabetes, the metabolic syndrome, insulin resistance, and other disorders responsive to PPARgamma activation including inflammatory disorders without causing fluid retention, edema, or congestive heart failure. Thus, angiotensin receptor blockers such as telmisartan and irbesartan can be surprisingly used to treat conditions that are known by those skilled in the art to be responsive to PPARgamma activators and can do so without causing fluid retention, edema, or congestive heart failure.

Because ARBs that increase the activity of PPARgamma do not cause substantial fluid retention and do not increase the risk for edema and CHF, they represent a significant improvement over the currently recognized drugs that increase the activity of PPARgamma. Specific examples of ARBs that increase the activity of PPARgamma are provided together with a description of novel clinical uses of these agents and instructions for such use. This invention also describes the fact that new ARBs can be developed that also increase the activity of PPARgamma or PPARgamma and PPARalpha. Such new ARBs will also be useful for treating or preventing type 2 diabetes, the metabolic syndrome, and other disorders responsive to administration of drugs that activate PPARs without promoting fluid retention, peripheral edema, pulmonary edema, or congestive heart failure.

Because the compounds of this invention also activate PPARs in addition to blocking the angiotensin II type 1 receptor, said compounds provide a more effective means of treating or preventing inflammatory and metabolic disorders including atherosclerosis than compounds that block the angiotensin II type 1 receptor but do not activate PPARs.

Also surprisingly, by administering an ARB or ACE inhibitor prior to or concurrently with compounds that activate PPARgamma either as separate pills or tablets or capsules, or by administering both drugs formulated in a single pill or tablet or capsule, one can also prevent or treat glucose intolerance or type 2 diabetes and other PPAR responsive disorders without causing fluid retention, edema, or congestive heart failure.

This invention relates to methods for treating or prophylactically preventing an inflammatory or metabolic disorder in a mammal (human or non-human) without causing, promoting, or aggravating fluid retention, peripheral edema, pulmonary edema, or congestive heart failure, by administering to a mammal in need thereof, a therapeutically effective amount of a compound sufficient to partially or fully activate peroxisome proliferator activated receptors (PPARs) and partially or fully inhibit, antagonize or block the activity of angiotensin II type 1 receptors.

In one embodiment the mammal is a human child, adolescent or adult and the therapeutically effective amount of the compound is used to prepare a medicament for treatment of the metabolic disorder in the human.

In one embodiment, said compound increases the activity of the PPAR subtype, PPARgamma or the PPARgamma-retinoid X receptor (PPARgamma-RXR) heterodimer, independently or in combination with an increase in activity of PPARalpha, PPARdelta, or both PPARalpha and PPARdelta.

In one embodiment said compound is administered in a pharmacologically acceptable form and in a therapeutically effective amount sufficient to prophylactically prevent, slow, delay or treat a metabolic disorder or disease selected from the group consisting of insulin resistance, glucose intolerance, impaired glucose tolerance, impaired fasting serum glucose, impaired fasting blood glucose, hyperinsulinemia, pre-diabetes, type 1 diabetes, type 2 diabetes mellitus, insulin-resistant hypertension, the metabolic syndrome, the metabolic hypertensive syndrome, (metabolic) syndrome X, the dysmetabolic syndrome, obesity, visceral obesity, hypertriglyceridemia, elevated serum concentrations of free fatty acids, elevated serum concentrations of C-reactive protein, elevated serum concentrations of lipoprotein(a), elevated serum concentrations of homocysteine, elevated serum concentrations of small, dense low-density lipoprotein (LDL)-cholesterol, elevated serum concentrations of lipoprotein-associated phospholipase (A2), reduced serum concentrations of high density lipoprotein (HDL)-cholesterol, reduced serum concentrations of HDL(2b)-cholesterol, and reduced serum concentrations of adiponectin.

In a particular embodiment, as described in U.S. Pat. No. 6,100,252 (Heterocyclic compounds and their use as angiotensin antagonists by Naka, et al.) the compound is of the general formula:

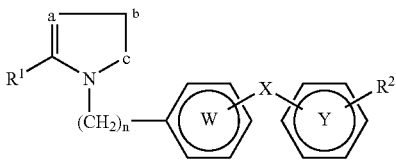

[wherein R1 is an optionally substituted hydrocarbon residue which is optionally bonded through a hetero-atom; R2 is an optionally substituted 5-7 membered heterocyclic residue having, as a group capable of constituting the ring, a carbonyl group, a thiocarbonyl group, an optionally oxidized sulfur atom or a group convertible into them; X is a direct bond or a spacer having an atomic length of two or less between the ring Y and the ring W; W and Y are independently an optionally substituted aromatic-hydrocarbon residue optionally containing a hetero-atom or an optionally substituted heterocyclic residue; n is an integer of 1 or 2; a and b forming the heterocyclic residue are independently one or two optionally substituted carbon or hetero atoms; c is an optionally substituted carbon or hetero atom; and, in the group of the formula:

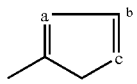

substituents on adjacent two atoms forming the ring are optionally bonded to each other to form a 5-6 membered ring together with the two atoms forming the ring] or a pharmaceutically acceptable salt thereof, or a pharmaceutically acceptable solvate thereof.

In one embodiment, the compound is formulated for oral administration. In another embodiment, the compound is formulated for topical administration.

In a preferred embodiment, the compound is telmisartan, or an analog thereof. In another preferred embodiment, the compound is irbesartan, or an analog thereof. In some embodiments, the total effective daily orally administered dose is selected from the range of from about 20 mg to 1000 mg.

The present invention further provides methods for screening compounds for treating or prophylactically preventing an inflammatory or metabolic disorder in a mammal by selecting a compound having the properties of: (a) at least partially activating peroxisome proliferator activated receptors (PPARs); and (b) at least partially inhibiting, antagonizing or blocking an activity of angiotensin II type 1 receptors. In some embodiments the method further includes selecting a compound that does not cause, promote, or aggravate fluid retention, peripheral edema, pulmonary edema, or congestive heart failure in the mammal.

DETAILED DESCRIPTION OF THE INVENTION

This invention relates to a method for preventing, delaying or treating insulin resistance, pre-diabetes, glucose intolerance, impaired glucose tolerance, the metabolic syndrome, type 2 diabetes, or other insulin resistance syndromes without causing systemic fluid retention, or increasing the risk for fluid retention, peripheral edema, pulmonary edema, or congestive heart failure by administering a compound that increases both the activity of peroxisome proliferator activated receptors and blocks/antagonizes activity of the angiotensin II type 1 receptor. This invention further relates to novel clinical uses of certain angiotensin II type 1 receptor blockers (ARBs) based on the discovery that said compounds can increase the activity of peroxisome proliferator activated receptors (PPARs), PPARγ, PPARα, or PPARδ, or any combination thereof, and can be used to treat and to prevent PPAR-regulated diseases and their complications including metabolic, inflammatory, proliferative, and cardiovascular diseases not previously recognized to be therapeutic targets for ARBs or more effectively than ARBs that do not activate PPARs. This invention further relates to methods for developing and using drugs that have the dual ability to block or inhibit activity of the renin-angiotensin-aldosterone system and to activate PPARs. Another aspect of this invention relates to methods for screening libraries of compounds to determine which are likely candidates for use in the practice of this invention.

DEFINITIONS

Body mass index (BMI) of a human patient is defined as the weight in kilograms divided by the square of the height in meters, such that BMI has units of $kg/m^2$.

Overweight is defined as the condition wherein the individual has a BMI greater than or 25 $kg/m^2$ and less than 30 $kg/m^2$.

Obesity is defined as the condition wherein the individual has a BMI equal to or greater than 30 $kg/m^2$. In another aspect, the term obesity is used to mean visceral obesity.

Visceral obesity is defined as a waist-to-hip ration of 1.0 in men and 0.8 in women, which, in another aspect defines the risk for insulin resistance and the development of pre-diabetes.

Euglycemia is defined as the condition in which a subject has a fasting blood glucose concentration within the normal range, greater than 70 mg/dl (3.89 mmol/L) and less than 110 mg/dl (6.11 mmol/L). The word fasting has the usual meaning as a medical term.

Impaired glucose tolerance (IGT), is defined as the condition in which a subject has a fasting blood glucose concentration or fasting serum glucose concentration greater than 110 mg/dl and less than 126 mg/dl (7.00 mmol/L), or a 2 hour postprandial blood glucose or serum glucose concentration greater than 140 mg/dl (7.78 mmol/L) and less than 200 mg/dl (11.11 mmol/L). The term impaired glucose tolerance is also intended to apply to the condition of impaired fasting glucose.

Hyperinsulinemia is defined as the condition in which a subject with insulin resistance, with or without euglycemia, in which the fasting or postprandial serum or plasma insulin concentration is elevated above that of normal, lean individuals without insulin resistance, having a waist-to-hip ration <1.0 (for men) or <0.8 (for women).

The terms "insulin-sensitizing", "insulin resistance-improving" or "insulin resistance-lowering" are synonymous and used interchangeably.

Insulin resistance is defined as a state in which circulating insulin levels in excess of the normal response to a glucose load are required to maintain the euglycemic state (Ford ES, et al. *JAMA*. (2002) 287:356-9). Insulin resistance, and the response of a patient with insulin resistance to therapy, may be quantified by assessing the homeostasis model assessment to insulin resistance (HOMA-IR) score, a reliable indicator of insulin resistance (Katsuki A, et al. Diabetes Care 2001;24:362-5). The estimate of insulin resistance by the homeostasis assessment model (HOMA)-IR score is calculated with the formula (Galvin P, et al. Diabet Med 1992;9:921-8):

HOMA-IR=[fasting serum insulin (µU/mL)]×[fasting plasma glucose (mmol/L)/22.5]

Patients with a predisposition for the development of IGT or type 2 diabetes are those having euglycemia with hyperinsulinemia and are by definition, insulin resistant. A typical patient with insulin resistance is usually overweight or obese.

The term pre-diabetes is the condition wherein an individual is pre-disposed to the development of type 2 diabetes. Pre-diabetes extends the definition of impaired glucose tolerance to include individuals with a fasting blood glucose within the high normal range ≧100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more $1^{st}$ degree relative with a diagnosis of IGT or type 2 diabetes. Insulin resistance can be confirmed in these individuals by calculating HOMA-IR score. For the purpose of this invention, insulin resistance is defined as the clinical condition in which an individual has a HOMA-IR score >4.0 or a HOMA-IR score above the upper limit of normal as defined for the laboratory performing the glucose and insulin assays.

Type 2 diabetes is defined as the condition in which a subject has a fasting blood glucose or serum glucose concentration greater than 125 mg/dl (6.94 mmol/L).

The metabolic syndrome, also called syndrome X (when used in the context of a metabolic disorder), also called the dysmetabolic syndrome is a syndrome complex with the cardinal feature being insulin resistance (Laaksonen D E, et al. *Am J Epidemiol* 2002;156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference >40 inches or 102 cm in men, and >35 inches or 94 cm in women
2. Triglycerides: ≧150 mg/dL
3. HDL-cholesterol<40 mg/dL in men
4. Blood pressure≧130/85 mm Hg (SBP≧130 or DBP≧85)
5. Fasting blood glucose≧110 mg/dL The NCEP definitions have been validated (Laaksonen D E, et al. *Am J Epidemiol*. (2002) 156:1070-7).

The term congestive heart failure (CHF) includes heart failure of any etiology, including but not limited to, heart failure with diastolic dysfunction, heart failure with systolic dysfunction, heart failure associated with cardiac hypertrophy, and heart failure that develops as a result of infectious myocarditis, inflammatory myocarditis, chemical myocarditis, cardiomyopathy of any etiology, hypertrophic cardiomyopathy, congenital cardiomyopathy, and cardiomyopathy associated with ischemic heart disease or myocardial infarction.

The term PPAR means one or any combination of PPARalpha, PPARgamma and PPARdelta.

The term PPARgamma means one or any combination of PPARgamma1, PPARgamma2, PPARgamma3.

The terms PPAR activator or PPARgamma activator means any compound that, by any mechanism, increases, or causes an increase in the activity of PPARgamma or the heterodimer of PPARgamma with the retinoid X receptor (RXR), either by direct binding to either PPARgamma or RXR or indirectly through any other mechanism that affects the ability of PPARgamma or the PPARgamma-RXR heterodimer to influence gene expression. Such PPAR activators may affect PPARgamma activity either alone or in combination with activation of other PPARs including either PPARalpha, PPARdelta, or both PPARalpha and PPAR delta.

A PPAR-dependent disease is a disease in which 1) administration of a PPAR ligand slows, ameliorates, stops or reverses the pathological process, and or 2) said disease is associated with impaired signal transduction upstream from PPAR and its interaction with the gene transcription machinery, and or 3) activation, partial activation or antagonism by a PPAR ligand (PPARα, PPARγ, PPARδ) leads to the prevention, amelioration, cure, or arrest of said disease or pathological process.

An angiotensin II-dependent disease is a disease in which: 1) administration of a AT1 receptor antagonist slows, ameliorates, stops or reverses the pathological process, and or 2) said disease is associated with impaired signal transduction within the RAAS system, and or 3) said disease is facilitated or exacerbated by activation of the AT1 receptor by angiotensin II, the initiating step being the by binding of angiotensin II the AT1 receptor. Because angiotensin II is a pro-inflammatory mediator, angiotensin II-dependent diseases are expected to be inflammatory in nature (Phillips M I, Kagiyama S. *Curr Opin Investig Drugs* 2002;3:569-77). ARBs have the potential to ameliorate inflammatory diseases, and because PPAR ligands also function as anti-inflammatory agents with differing mechanisms of action, dual ARB/PPAR ligands would have novel, more potent, synergistic effects on inflammatory diseases (Tham D M, et al. Physiol Genomics 2002;11:21-30).

An inflammatory disease is a disease associated dysfunction of the immune system, exemplified as, but not limited to: 1) increased production of inflammatory cytokines (interleukin(IL)-1beta, IL-2, IL-6, IL-8, IL-12, tumor necrosis factor-α, interferon-γ, monocyte chemoattractant protein-1), 2) increased conversion of Th2 lymphocytes to the Th1 phenotype or increased Th1/Th2 ratio, 3) inappropriate function of NK (killer) T lymphocytes resulting in autoantibodies and lack of "self" recognition resulting in an autoimmune disease, 4) increased expression or activation of inflammatory nuclear transcription factors (NFAT, NF-κB, AP-1, JNK/STAT), 5) increased expression of iNOS.

A proliferative disease is a disease associated with: 1) pathological proliferation of normally quiescent cells, 2) pathological migration of cells from their normal location (e.g. metastasis of neoplastic cells), 3) pathological expression of proteolytic enzymes such as the matrix metalloproteinases (collagenases, gelatinases, elastases), 4) pathological angiogenesis as in proliferative retinopathy and tumor metastasis.

Angiogenesis is the process by which normally quiescent endothelium responds to physiological or pathological stimuli (such as proliferating endometrium, injury, tumor growth, or diabetic retinopathy) resulting in pathological proliferation of blood vessels (neovascularization). Pathological angiogenesis (neovascularization) is an unregulated, unbridled process resulting as in inappropriate vascular proliferation as in tumor neovascularization, lymphangiogenesis, and tumor metastasis.

A degenerative disease is a disease associated with deterioration or destruction normal tissue, resulting from immune dysregulation resulting in the upregulation of one or more inflammatory nuclear transcription factors, inflammatory cytokines and other inflammatory molecules such as proteases (e.g. MMP-9) and iNOS, leading to pathological degeneration of the respective cell or tissue or organ which is the therapeutic target.

The term heart failure includes congestive heart failure, heart failure with diastolic dysfunction, heart failure with systolic dysfunction, heart failure associated with cardiac hypertrophy, and heart failure that develops as a result of chemically induced cardiomyopathy, congenital cardiomyopathy, and cardiomyopathy associated with ischemic heart disease or myocardial infarction.

The current invention relates to the surprising discovery that certain ARBs can also function as PPARgamma activators and can be used to prevent, delay, slow, arrest or treat insulin resistance, pre-diabetes, glucose intolerance, impaired glucose tolerance, the metabolic syndrome, type 2 diabetes, or other insulin resistance syndromes, as well as other disorders responsive to PPAR activators without increasing the risk for fluid retention, peripheral edema, pulmonary edema, or congestive heart failure. Thus, the current invention provides novel uses for certain ARBs for the treatment or prevention of diseases known to be responsive to drugs that increase PPARgamma activity including metabolic, endocrine, proliferative, autoimmune, immunomodulatory and inflammatory diseases and certain infective diseases. Accordingly, the present invention includes the discovery of how to make, identify, and use drugs that activate PPARgamma and that do not increase the risk of fluid retention, edema, or congestive heart failure like existing drugs that activate PPARgamma. This invention describes the discovery that it is possible to make and use compounds that have the dual ability to block or inhibit the renin-angiotensin-aldosterone system and the ability to activate PPARgamma. The invention provides specific examples of such compounds not previously recognized to have this dual ability and shows that these compounds can be used to treat conditions not previously known to be responsive to such compounds. Thus, this invention includes the surprising discovery that one can use certain to treat disorders responsive to treatment with PPAR activators.

The present invention provides novel uses for ARBs that also activate PPARs for the treatment or prevention of diseases known to be responsive to PPAR ligands, in particular PPARgamma partial agonists or PPARgamma full agonists. Target diseases include metabolic, endocrine, proliferative, degenerative, autoimmune, atopic, and inflammatory diseases. The present invention also relates to the identification of novel or previously unknown ARBs that also activate PPARgamma and have a reduced propensity for causing fluid retention, edema, or congestive heart failure compared to other activators of PPARgamma. Thus, the present invention includes the discovery of how to identify compounds that block the rennin-angiotensin system and, at the same time, activate PPARgamma but have a significantly lower risk of causing fluid retention, edema, or congestive heart failure. The invention provides specific examples of ARBs not previously recognized to have this dual ability and reveals why these compounds can be used to treat conditions not previously known to be responsive to said compounds. Thus, this invention includes the surprising discovery that one can use certain ARBs for the purpose of treating or preventing disorders responsive to treatment with PPAR ligands, said ligands having improved safety and therapeutic efficacy.

This invention relates to the unpredictable and surprising discovery that certain compounds can block the renninangiotensin system by antagonizing the AT1 receptor while activating PPARs, in particular, PPARgamma.

In another aspect this invention relates to novel clinical uses of ARBs in the prevention and treatment of PPAR-responsive conditions or diseases.

In another aspect this invention relates to novel clinical uses of ARBs in the prevention and treatment of PPAR-related conditions or diseases mediated through PPAR-dependent regulation of or interaction with related nuclear receptors, including the retinoid X receptor (RXR), retinoid orphan-related receptor (ROR), liver X receptor (LXR), farnesoid X receptor (FXR), vitamin D receptor (VDR), estrogen receptors (ER-alpha and ER-beta), glucocorticoid receptor (GR), thyroid receptor (TR) and androgen receptor (AR).

In another aspect this invention relates to design and identification of those ARBs that modulate the activity of PPARs, thus providing for safer and enhanced therapeutic efficacy for preventing or treating PPAR-mediated conditions or diseases, or the end-organ complications of these diseases.

In another aspect, this invention relates to the identification of low toxicity PPAR ligands that are effective ARBs or ACE inhibitors by screening with AT1 receptor binding assays.

In another aspect, this invention relates to methods for identifying ARBs or derivatives thereof, that can be made to further enhance their ability to activate PPAR and to more effectively treat PPAR-responsive or PPAR-mediated diseases, disorders or conditions.

Compounds according to the present invention have renoprotective effects and are more effective for treating renal diseases or limiting the rate of progression of renal diseases (e.g. glomerular nephritis, glomerulosclerosis, nephrotic syndrome, hypertensive nephrosclerosis, polycystic kidney diseases, and diabetic nephropathy) compared to compounds that do not have this dual ability to inhibit the activity of the renin angiotensin aldosterone system and to activate PPARs.

This invention identifies ARBs that can be used as monotherapy, or in combination with one or more other pharmacological agents, or as adjunctive therapy to prevent, delay, slow, arrest or treat:

1. Metabolic diseases associated with insulin resistance such as impaired glucose tolerance, glucose intolerance, pre-diabetes, the metabolic syndrome (also termed metabolic syndrome X or the dysmetabolic syndrome), obesity, type 2 diabetes mellitus, gestational diabetes, polycystic ovarian syndrome, Werner's syndrome;

2. Dyslipidemias associated with hyperlipemia, elevated free fatty acids, hypercholesterolemia, hypertriglyceridemia, elevated low density lipoprotein-(LDL)-cholesterol, elevated very low density lipoprotein-(VLDL)-cholesterol, elevated intermediate density lipoprotein-(IDL)-cholesterol, or reduced high density lipoprotein-(HDL)-cholesterol;

3. Inflammatory skin diseases such as psoriasis, atopic dermatitis, seborrheic dermatitis, solar dermatitis;

4. Inflammatory or proliferative diseases such as atherosclerosis, atherogenesis, vascular stenosis or restenosis, rheumatoid arthritis, ulcerative colitis, Crohn's disease, endometriosis;Inflammatory, neurodegenerative or neuropsychiatric diseases such as Alzheimer's disease, Parkinson's disease, multiple sclerosis, depression, psychoses;Benign, malignant tumor or metastatic tumor growth;

5. Neovascularization and pathological angiogenesis associated with neoplasia, tumor growth and metastasis;

6. Inflammatory or proliferative ocular diseases including corneal angiogenesis, chorio-retinal retinopathy, age-related macular degeneration and neovascularization, uveitis, glaucoma, iritis, keratitis, retinitis;

7. Pro-thrombotic diseases as in hypercoagulable or thrombotic states, such as diseases associated with elevated plasminogen activator inhibitor-1 (PAI-1), thombotic or thromboembolic diseases, atheroma formation;

8. Autoimmune diseases such as type 1 diabetes mellitus, multiple sclerosis, Parkinson's disease, amyotropic lateral sclerosis;

9. Allograft rejection upon or subsequent to transplantation, and complications associated with both acute and chronic allograft rejection;

10. Infective diseases caused by DNA viruses, RNA viruses and retroviruses, including AIDS, SARS and hepatitis C;

11. Infective diseases caused by prions, such as kuru, Cretzfeld-Jackob disease and spongiform encephalopathies;

12. Complications associated with viral and prion-related infections, including CNS-related complications and CNS-related degenerative conditions that result in encephalopathy, dementia and cachexia;

13. Cachexia associated with chronic diseases such as CHF, cancer, multiple sclerosis, chronic infections, anorexia nervosa, bullemia;

14. CD-36 mediated diseases such as certain metabolic diseases, retinitis pigmentosa and malaria 15. Conditions such as obesity, including methods for controlling appetite or food intake, diet and anorexia.

A compound or a pharmaceutical composition according to the present invention is a PPARgamma activator which has less toxicity than other PPAR activators of the current art. Less toxicity principally refers to substantially reduced potential for fluid retention, edema or heart failure. Said compound or pharmaceutical composition according to the present invention may also be used prevent, delay, slow, arrest or treat chronic medical pathologies and diseases, including: a) diabetic complications and diabetes-associated conditions including steatohepatitis, neuropathy, nephropathy, retinopathy, chorioretinopathy, choroidal neovascularization, retinal neovcascularization, macular degeneration, retinal detachment, glaucoma, cataract, microangiopathy, atherosclerosis, ischemic heart disease, ischemic cerebrovascular disease, stroke, peripheral arteriosclerosis, cerebral arteriosclerosis, coronary arteriosclerosis, hyperinsulinemia-induced sensory disorder, obesity, heart failure, myocardial infarction, angina pectoris, cerebral infarction, chronic cardiomyopathy, cardiac fibrosis, renal disorders, glomerular nephritis, glomerulosclerosis, nephrotic syndrome, hypertensive nephrosclerosis, terminal renal disorders, microangiopathy, atherosclerosis, ischemic heart disease, ischemic cerebrovascular disease, diabetic cachexia, and the like; b) cachexia resulting from chronic diseases or conditions including carcinomatous cachexia, hemophathic cachexia, endocrinopathic cachexia, infectious cachexia, cachexia induced by acquired immunodeficiency syndrome, cachexia associated with congestive heart failure or chronic cardiomyopathy, anorexia nervosa, and the like; c) degenerative diseases including osteopenia, osteoporosis, muscular dystrophy, rheumatoid arthritis, spondylitis deformans, osteoarthritis, lumbago, gout, neuralgia, gastritis, hepatitis, pneumonia, pancreatitis and the like. In addition, a compound according to the invention may also be employed as a pharmaceutical for controlling appetite or food intake, diet and anorexia.

A compound or a pharmaceutical composition according to the present invention has a blood sugar reducing effect, a blood lipid reducing effect, a blood insulin reducing effect, an insulin sensitivity enhancing effect, an insulin resistance improving effect, a body weight reducing effect, a central body girth (measured as waist:hip ratio) reducing effect, a body fat mass reducing effect, through effects on PPAR-gamma activity, PPARgamma-RXR, or through effects on relater nuclear receptors, including FXR, LXR, ROR, cAMP-response element-binding protein (CREB), CREB-binding protein (CBP), CBP/p300, sterol regulatory binding proteins (SREBPs), steroid receptor coactivator-1 (SRC-1), PPARgamma coactivator-1alpha (PGC-1alpha), PPAR-gamma coactivator-1beta (PGC-1beta) and PPAR-binding protein (PBP).

While the dose of a compound or a pharmaceutical composition according to the present invention varies depending on various factors such as the subject to be treated, the administration route, the disease or the condition to be treated, a compound according to the present invention as an active ingredient may for example be given orally to an human at a daily dose of about 0.05 to 100 mg/kg body weight, preferably about 0.1 to 10 mg/kg body weight, preferably one to three times a day, with a single dose providing therapeutic efficacy for at least 24 hr being preferred. It is also contemplated that the therapies described in the present invention is applicable to children and adults.

A compound according to the present invention has a blood sugar reducing effect, a blood lipid reducing effect, a blood insulin reducing effect, an insulin sensitivity enhancing effect, an insulin resistance improving effect, a body weight reducing effect, a central body girth (measured as waist:hip ratio) reducing effect, a body fat mass reducing effect, through ligand-dependent PPAR activity or PPAR-related nuclear receptor function activities. A PPAR is a nuclear transcription factor, and the term is used here to encompass PPARγ, PPARα, PPARδ nuclear receptors that function as DNA-binding transcription factors having as a secondary modulating ligand for a dimeric nuclear receptor partner, such as an oil-soluble vitamin (vitamin A, vitamin D), a retinoid, or steroid hormone, and may be any of a monomer receptor, a homodimer receptor and a heterodimer receptor. A monomer receptor is exemplified by retinoid O receptor (hereinafter abbreviated occasionally as RORα (GenBank Accession No.L14611) RORβ (GenBank Accession No.L14160), RORγ (GenBank Accession No.U16997); Rev-erbα (GenBank Accession No.M24898), Rev-erbβ. (GenBank Accession No.L31785); ERRα (GenBank Accession No.X51416), ERRβ (GenBank Accession No.X51417); Ftz-FIα (GenBank Accession No.S65876), Ftz-FIβ. (GenBank Accession No.M81385); TIx (GenBank Accession No.S77482); GCNF (GenBank Accession No.U14666) and the like. A homodimer receptor may for example be a homodimer formed from retinoid X receptor (hereinafter abbreviated occasionally as RXRα (GenBank Accession No.X52773), RXRβ. (GenBank Accession No.M84820), RXRγ. (GenBank Accession No.U38480); COUPα (GenBank Accession No.X12795), COUPβ (GenBank Accession No.M64497), COUPγ (GenBank Accession No.X12794); TR2α (GenBank Accession No.M29960), TR2β (GenBank Accession No.L27586); or, HNF4α (GenBank Accession No.X76930), HNF4.γ. (GenBank Accession No.Z49826) and the like. A heterodimer receptor may for example be a heterodimer formed from retinoid receptor X (RXRα, RXRβ or RXRγ) described above together with one receptor selected from the group consisting of retinoid A receptor (hereinafter abbreviated occasionally as RARα (GenBank Accession No.X06614), RARβ (GenBank Accession No.Y00291), RARγ (GenBank Accession No.M24857); a thyroidal hormone receptor (hereinafter abbreviated occasionally as TRα (GenBank Accession No.M24748), TRβ (GenBank Accession No.M26747); a vitamin D receptor (VDR) (GenBank Accession No.J03258); a peroxisome proliferator-activated receptor (hereinafter abbreviated occasionally as PPARα (GenBank Accession No.L02932), PPARβ (PPARdelta) (GenBank Accession No.U10375), PPARγ (GenBank Accession No.L40904); LXRα (GenBank Accession No.U22662), LXRβ (GenBank Accession No.U14534); FXR (GenBank Accession No.U18374); MB67 (GenBank Accession No.L29263); ONR (GenBank Accession No.X75163; and NUR.α (GenBank Accession No.L13740), NUR.β. (GenBank Accession No.X75918), NUR.γ. (GenBank Accession No.U12767).

The current invention constitutes the surprising finding that certain ARBs can activate PPARγ, promote adipogenesis, lower (improve) insulin resistance, and can be used to treat or prevent the metabolic syndrome and components thereof (see definitions) and type 2 diabetes. Among the ARBs presently approved for human use telmisartan and irbesartan are specific examples of compounds of this invention, and can surprisingly be used to treat or prevent insulin resistance, the metabolic syndrome and type 2 diabetes (i.e. lower hyperinsulinemia and/or hyperglycemia), lower triglycerides, and elevate HDL-cholesterol. An extension of this invention is the predictive design of derivatives of existing ARBs to improve their insulin resistance-lowering activity by increasing the EC50 for activation of PPARγ.

It has been previously shown that the risk for diabetes in patients given ARBs is lower than that in patients given other antihypertensive drugs. However, until the current discovery described herein, it was not known that these drugs could activate PPARγ and it could not have been predicted that these drugs could be used to treat insulin resistance syndromes such as type 2 diabetes or other conditions known to be treatable by PPAR ligands. For example, the lower risk of diabetes reported in patients given ARBs versus β-blockers (Dahlof B, et al. Lancet 2002; 359:995-1003) could have been due to the fact that β-blockers aggravate insulin resistance and therefore, the results of clinical studies comparing ARBs to other agents cannot be used to predict whether ARBs can be used to treat diabetes or other disorders responsive to PPARγ ligands.

Because ARBs do not cause substantial fluid retention and do not increase the risk for edema and heart failure, they represent a significant improvement over the currently recognized PPAR ligands. Specific examples of ARBs that activate PPARγ are provided together with a description of novel clinical uses of these agents and instructions for such use. This invention also describes the novel finding that one can derive new ARBs with greater ability to activate PPARs than existing ARBs and that such ARBs with enhanced ability to activate PPARs can be used to prevent or treat clinical disorders known to be responsive to PPAR ligands without causing the degree or extent of side effects of fluid retention, edema, or congestive heart failure caused by currently marketed PPAR ligands. Surprisingly, one can also make modifications to currently available ARBs that will significantly enhance their ability to activate PPARs and therefore enhance their ability to treat disorders known to be responsive to PPAR ligands. Such compounds also represent an improvement over existing ARBs as they have greater ability to activate PPARs and therefore have the added benefits of improving clinical disorders that are responsive to treatment with PPAR activators. Using the methods of this invention, one can identify, develop, and use PPAR ligands that have the ability to inhibit ACE activity or block angiotensin receptors. Such compounds represent a novel approach to treating disorders known to be responsive to PPAR ligands because they do not promote fluid retention, edema, or congestive heart failure to the extent that currently available PPAR ligands are know to do.

Specific examples of ARBs that activate PPARγ are provided together with a description of novel clinical uses of these agents and instructions for such use. This invention also describes the novel finding that one can derive new ARBs with greater ability to activate PPARs than existing ARBs and that such ARBs, having enhanced ability to activate PPARs, can be used to prevent or treat clinical disorders known to be responsive to PPAR ligands without causing the degree or extent of side effects of fluid retention, edema, or congestive heart failure as do currently marketed PPARγ ligands. Surprisingly, one can structurally modify currently available ARBs to significantly enhance their ability to activate PPARs and therefore enhance their ability to treat disorders known to be responsive to PPAR ligands. Such compounds also represent an improvement over existing ARBs in that they more effectively activate PPARs and therefore have the added benefits of improving clinical disorders that are responsive to treatment with PPAR activators. Using the methods of this invention, one can identify, develop, and use PPAR ligands that have the ability to antagonize the AT1 receptor. Such compounds represent a novel approach to treating disorders known to be responsive to PPAR ligands because they do not promote fluid retention, edema, or congestive heart failure to the extent that currently available PPAR ligands are know to do. While not wishing to be bound by theory, PPARγ ligands cause fluid retention through a number of mechanisms. A surprising feature of this invention is that the fluid retention usually caused by PPARγ ligands can be prevented or attenuated by blockade of AT1 receptors. Because blockade of the AT1 receptor does not always attenuate or prevent fluid retention in some animal models treated with PPARγ ligands, and because multiple mechanisms may be involved in the fluid retention caused by PPARγ ligands, it could not have been predicted that blockade of AT1 receptors could prevent or attenuate the fluid retention caused by PPARγ ligands in humans. Also surprisingly, by administering an ARB prior to or concurrently with compounds that activate PPARgamma either as separate pills or tablets, or by administering both drugs formulated in a single pill or tablet, one can also treat glucose intolerance or type 2 diabetes and other PPAR responsive disorders without causing fluid retention, edema, or congestive heart failure.

Because PPARγ is not recognized to be structurally related to the AT1 receptor, ARBs would not be expected to activate PPARγ. Thus, it could not have been predicted that one could use any existing ARB to activate PPARγ. Therefore, one could not have predicted that ARBs would be useful to treat disorders responsive to PPARγ ligands or that one could design drugs that have the ability to block the AT1 receptor while also having the ability to activate PPARγ. This invention describes the surprising discovery that compounds can be designed to antagonize the AT1 receptor while also possessing the ability to activate PPARγ, and that such compounds can be surprisingly useful for treating conditions known to be responsive to PPARγ ligands without promoting fluid retention, edema, or heart failure. Also surprisingly, by administering an ARB that also activates PPARγ, one can also treat insulin resistance, the metabolic syndrome, glucose intolerance, type 2 diabetes, polycystic ovarian syndrome, as well as other PPARγ-responsive disorders without causing fluid retention, edema, or congestive heart failure. These findings suggested that like the antidiabetic thiazolidinedione PPARγ agonists, telmisartan may also improve insulin resistance. We determined that administration of telmisartan to a patient with the metabolic syndrome improved insulin resistance as determined by reduction of the HOMA-IR score (see definitions). When administered to a patient with type 2 diabetes, telmisartan lowered the hyperglycemia, lowers plasma triglycerides, and elevated blood HDL-cholesterol. These finding led to the surprising discovery, and invention, that ARBs that also activate PPARγ are useful for preventing and treating the metabolic syndrome, type 2 diabetes, and improving lipid metabolism by lowering triglycerides and elevating HDL-cholesterol. These insulin-sensitizing, antidiabetic effects are limited to certain ARBs, such as telmisartan and irbesartan. ARBs such as valsartan and eprosartan which do not activate PPARγ at doses reasonably achievable at therapeutic doses, did not promote adipogenesis, a property of telmisartan and the insulin-sensitizing thiazolidinedione PPARγ agonists. Thus, the property of reducing insulin resistance is restricted within the class of non-peptide ARBs known as "sartans", and are unpredictable surprising and non-obvious. This invention discloses methods of determining which "sartans" or other AT1 receptor antagonists may function as an insulin-sensitizing, insulin resistance-improving or anti-diabetic agent.

Insulin resistant states predispose to inflammatory, proliferative and degenerative diseases such as atherosclerosis, atherogenesis, vascular stenosis or restenosis after invasive intravascular procedures, cardiomyopathy, and myocardial fibrosis. Moreover, the excessive use of glucocorticoids and/or immunosuppressive agents, as in the treatment of chronic inflammatory diseases and complications of immunosuppression in allograft rejection, such as osteoporosis, Cushing's disease, lipodystrophy, insulin resistance, type 2 diabetes, hyperlipidemia, transplantation-related hypertension, atherosclerosis, renal disease, arteritis and endarteritis. This invention predicts that administration of an ARB that also activates PPARγ would result in the clinical improvement of these conditions.

Uses of the Invention

The methods of treatment provided by this invention are practiced by administering to a human or vertebrate animal in need a dose of a compound, or a pharmaceutically acceptable salt, ester, solvate or tautomer thereof, that blocks or antagonizes the angiotensin II type 1 receptor and activates either PPARgamma alone or in combination with PPARalpha, or PPARdelta both PPARalpha and PPAR gamma. In another aspect, the novel compounds used to practice this invention are set forth above. The specific diseases and associated disorders that can be treated with the compounds described in this invention are listed in Tables I through X.

TABLE I

Examples of dermatological disorders and inflammatory skin disorders treatable using compounds of this invention Kertinizing skin diseases, keratitis, hidradenitis, ichthyosis, melasma
Psoriasis (all forms, including p. vulgaris, p. guttata, p. discoidea, p. anthropica, p. universalis)
Acne (all forms, including a. vulgaris, a. rosacea, a. inversa, cystic acne)
Warts, verruca (all forms, including common warts, anogenital (venereal) warts, viral warts including human papilloma virus (HPV) infections, conjunctival warts, oral/buccal warts)
Acute and chronic dermatitides (inflammation of the skin), atopic dermatitis, allergic dermatitis, contact dermatitis, cosmetic dermatitis, chemical dermatitis, seborrheic dermatitis, solar dermatitis, acute and chronic eczema, diaper rash, sunburn
Lupus associated skin lesions
Keratoses such as seborrheic keratosis, senile keratosis, actinic keratosis, photo-induced keratosis, skin aging, thinning skin, dry skin, wrinkle formation, photo-induced skin aging, keratosis follicularis
Keloids and prophylaxis against keloid formation
Leukoplakia, lichen planus
Urticaria, pruritus
Androgenic alopecia in men and women, hirsutism in women

TABLE II

Examples of psychiatric disorders treatable using compounds described in this invention Depression, primary depression or depression secondary to chronic diseases and medications
Dysphoric mood disorders
Obsessive compulsive disorder
Dysthymic disorders
Manic depressive (unipolar or bipolar) disorder
Anxiety states including panic disorder and agoraphobia
Post menstrual syndrome
Schizophrenia
Chronic fatigue syndrome
Substance abuse and drug addiction
Anorexia nervosa and anorexia bullemia

TABLE III

Examples of neurological/neurodegenerative disorders and CNS inflammatory disorders treatable using compounds described in this invention Migraine headaches (e.g. vascular headaches, common migraine)
Primary (e.g. Alzheimer's disease) and secondary (e.g. HIV-related) dementias
Degenerative CNS diseases (e.g. Parkinson's disease, amyotropic lateral sclerosis)
Demyelinating diseases (e.g. multiple sclerosis, Guillain-Barre syndrome)
Pain disorders including algesia, hyperalgesia, acute and chronic pain, allodynia
Primary and secondary encephalitis and encephalomyelitis (e.g. autoimmune encephalomyelitis, allergic encephalomyelitis)
Primary and secondary neuritis, autoimmune neuritis
Other autoimmune diseases (e.g. myesthenia gravis, Eaton-Lambert syndrome)
Congenital and secondary ataxias

TABLE IV

Examples of inflammatory and metabolic disorders associated with allograft transplantation treatable using compounds described in this invention The compounds described herein are useful as monotherapy or adjunctive therapy with existing immunosuppressive agents for the promotion and maintenance of allograft survival, post-transplantation.
Examples of inflammatory and proliferative conditions or diseases associated with allograft transplantation and immune suppression include:

1. Acute allograft rejection
2. Chronic allograft rejection
3. Graft versus host disease
4. Post-transplantation de novo malignancy (e.g. lymphoma and epidermal cancers)
5. Osteoporosis and osteopenia
6. Hyperlipidemia
7. Insulin resistance and diabetes mellitus
8. Hypertension
9. Atherosclerosis
10. Endarteritis associated with heart allograft transplantation
11. Glomerulonephritis associated with renal allograft transplantation
12. Cardiomyopathy and congestive heart failure associated with allograft transplantation, in particular heart transplantation

TABLE V

Examples of diseases of various organ systems treatable using compounds described in this invention

| Organ System | Disease/Pathology |
| --- | --- |
| Cardiovascular | Metabolic disorders including hypertension, vasculo-occlusive diseases including atherosclerosis, arteritis, endarteritis, endocarditis, myocarditis, arterial plaque (fibrous cap) rupture, thrombosis, restenosis after any invasive vascular procedures; acute coronary syndromes such as unstable angina, myocardial infarction, myocardial ischemia and other ischemic cardiomyopathies, non-ischemic cardiomyopathies, post-myocardial infarction cardiomyopathy and myocardial fibrosis, drug-induced cardiomyopathy. |
| Endocrine | Metabolic disorders including obesity, type 1 diabetes mellitus, type 2 diabetes mellitus, gestational diabetes, impaired glucose tolerance, Cushing's syndrome (e.g. secondary to chronic glucocorticoid therapy), polycystic ovarian syndrome, osteoporosis, osteopenia, accelerated aging of tissues and organs, e.g. Werner's syndrome. |
| Urogenital | Prostatitis, endometritis, endometriosis, benign prostatic hypertrophy, leiomyoma, polycystic kidney disease (e.g. autosomal dominant PKD), acute tubular necrosis, nephrotic syndrome, diabetic nephropathy, glomerulonephritis, erectile dysfunction in men and women |
| Pulmonary | Asthma, chronic obstructive pulmonary disease (COPD), reactive airway disease, pulmonary fibrosis, pulmonary hypertension. |
| Connective tissue | Rheumatoid arthritis, Raynaud's phenomenon/disease, Sjogren's syndrome, systemic sclerosis, systemic lupus erythematosus, |
| Joint | inflammatory bowel disease (ulcerative colitis, Crohn's disease) vasculitides, ankylosing spondylitis, osteoarthritis, reactive arthritis, psoriatic arthritis, fibromyalgia, osteoarthritis, sarcoidosis. |
| Liver/Other | Hepatic fibrosis, hepatic cirrhosis, hepatic steatosis, all etiologies, e.g. alcohol-induced (e.g. ethanol), drug-induced (e.g. tylenol), and toxin-induced (e.g. mushroom poisoning) Fibrocystic breast disease, fibroadenoma, endometriosis |

TABLE VIa

Examples of neoplastic diseases treatable using compounds described in this invention

| Organ System | Malignancy/Cancer type |
| --- | --- |
| Skin | Basal cell carcinoma, melanoma, squamous cell carcinoma; cutaneous T cell lymphoma; Kaposi's sarcoma. |
| Hematological | Acute leukemia, chronic leukemia and myelodysplastic syndromes. |
| Urogenital | Prostatic, renal and bladder carcinomas, anogenital carcinomas including cervical, ovarian, uterine, vulvar, vaginal, and those associated with human papilloma virus infection. |
| Neurological | Gliomas including glioblastomas, astrocytoma, ependymoma, medulloblastoma, oligodendroma; meningioma, pituitary adenoma, neuroblastoma, craniopharyngioma. |
| Gastrointestinal | Colon, colorectal, gastric, esophageal, mucocutaneous carcinomas. |
| Breast | Breast cancer including estrogen receptor and progesterone receptor positive or negative subtypes, soft tissue tumors. |
| Metastasis | Metastases resulting from all neoplasms. |
| Other | Angiomata, angiogenesis associated with the neoplasms. |

TABLE VIb

Examples of neoplastic diseases treatable using compounds described in this invention (cont'd)

| Location | Malignancy/Cancer type |
| --- | --- |
| Various | fibrosarcoma, myxosarcoma, liposarcoma, chondrosarcoma, osteogenic sarcoma, chordoma, angiosarcoma, enthotheliosarcoma, lymphangiosarcoma, lymphangioendotheliosarcoma, synovioma, mesothelimoa, Ewing's tumor, leiomyosarcoma, rhabdomyosarcoma, colon carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. |

TABLE VII

Examples of viral infections and related pathologies treatable according to the methods of this invention

| Virus | Viral infection/cancer or other virus-associated pathology |
| --- | --- |
| HTLV | T-cell leukemia/lymphoma, HTLV-associated arthritides/myelopathies. |
| HPV | Cervical and anogenital cancers; common and anogenital (venereal) warts, including verrucae, condyloma or condyloma acuminata, related non-neoplastic (e.g., keratitis, conjunctivitis) pre-neoplastic and neoplastic (e.g., conjunctival epithelial neoplasms) diseases of the eye. |
| HAV, HBV, HCV | Hepatitis, hepatocellular carcinoma, lymphoma. |
| CMV | Hepatitis, retinitis, meningitis. |
| HSV, VSV | Related mucocutaneous, oropharyngeal and genital diseases, related skin and respiratory infections, varicella-zoster, chicken pox, herpes zoster, post-herpetic neuralgia, conjunctivitis, keratoconjunctivitis, keratitis. |
| HHV | Exanthem subitum, infectious mononucleosis. |
| EBV | Infectious mononucleosis, chronic fatigue syndrome, lymphoma, conjunctivitis, keratitis, and related infections of the eye. |
| Adenoviruses | Upper and lower respiratory tract infections, pneumonia, conjunctivitis. |

TABLE VII-continued

Examples of viral infections and related pathologies treatable according to the methods of this invention

| Virus | Viral infection/cancer or other virus-associated pathology |
|---|---|
| RSV | Upper and lower respiratory tract infections, pneumonia. |
| PMV | Mumps and related manifestations, e.g., conjunctivitis. |
| MV, RV | Measles, Rubella ("German measles") and related manifestations. |
| Coxsackie viruses | Conjunctivitis, diabetes mellitus, respiratory infections. |
| Influenza viruses | Upper and lower respiratory tract infections, pneumonia. |

HIV, Human Immunodeficiency Virus; HTLV, Human T-cell Lymphocyte Virus; HPV, Human Papilloma Virus; HAV, Hepatitis A Virus; HBV, Hepatitis B Virus; HAV, Hepatitis C Virus; CMV, Cytomegalovirus; HSV, Herpes Simplex Virus (Types I & II); HHV, Human Herpes Virus; EBV, Epstein-Barr Virus; RSV, Respiratory Syncytial Virus; VZV, Varicella-Zoster Virus; PMV, Paramyxovirus; MV, Measles (Rubeola) Virus; RV, Rubella Virus

TABLE VIII

HIV related infections and diseases treatable using compounds described in this invention

| Organ system | Viral infection/manifestation or other HIV-associated disease |
|---|---|
| Immunologic | AIDS, primary HIV infection. |
| Dermatological | Anogenital cancers including rectal and cervical cancer, Kaposi's sarcoma, atopic dermatitis, squamous cell carcinoma, hairy leukoplakia, molluscum contagiosum, warts (HPV infections), seborrheic dermatitis, psoriasis, xeroderma, HSV and varicella-zoster infections. |
| Hematologic | Non-Hodgkin's lymphoma, B cell lymphoma, anemia, neutropenia, thrombocytopenia. |
| Gastrointestinal | Anorexia, gastroparesis, diarrhea, malabsorption, gastrointestinal CMV infections, esophagitis, colitis, hepatitis, lymphoma. |
| Ophthalmic | Conjunctivitis, keratitis, keratoconjunctivitis, uveitis, retinitis, chorioretinitis, CMV retinitis, iridocyclitis, vitreitis, choroiditis, papilledema, Kaposi's sarcoma, lymphoma, ocular palsies, conjunctival warts, pre-neoplastic and neoplastic diseases of the eye. |
| Cardiac | Myocarditis, endocarditis, pericarditis. |
| Pulmonary | CMV pneumonitis, lymphoid interstitial pneumonitis. |
| Nephrologic | HIV nephropathy, renal cell carcinoma, amyloidosis, uropathy. |
| Rheumatologic | Arthralgia, fibromyalgia, Reiter's syndrome, psoriatic arthritis, vasculitis. |
| Neurologic | Dementia, viral meningitis, viral encephalitis, HIV encephalopathy, progressive multifocal leukoencephalopathy, CNS lymphoma, peripheral and autonomic neuropathies. |
| Psychiatric | Dysphoric mood disorders, depression, depression associated with chronic diseases and medications, bipolar disorder, anxiety disorders, chronic fatigue syndrome, chronic pain, psychoses, substance abuse disorders and drug addiction. |
| General | Lymphoma, metastatic lymphoma, Kaposi's sarcoma, wasting syndrome, psychosis. |

TABLE IXa

Diseases of the eye treatable using compounds described in this invention

| Disease | virus |
|---|---|
| 1. Inflammatory eye diseases associated with viral infections | |
| Blepharitis | HSV, VZV, Vaccinia, HPV, molluscum contagiosum |
| Conjunctivitis | HSV, VZV, EBV, Adenovirus, Vaccinia, Variola, HPV, molluscum contagiosum, influenza |
| Follicular c. | Newcastle, measles, mumps, rubella, molluscum contagiosum |
| Hemorrhagic c. | Enterovirus, coxsackie |
| Catarrhal c | Rubella |
| Keratitis | HSV, VZV, EBV, Adenovirus, Vaccinia, Variola, HPV, molluscum contagiosum |
| Keratoconjunctivitis | HSV, VZV, EBV, Adenovirus, Vaccinia, Variola, HPV, molluscum contagiosum |
| Retinitis | CMV |
| Uveitis | HPV |

TABLE IXa-continued

Diseases of the eye treatable using compounds described in this invention

| Disease | virus |
|---|---|
| Conjunctival warts | HPV |
| Epithelial neoplasms | HPV |

2. Oularplastic diseases

| | |
|---|---|
| Benign tumors | Keratocanthoma, molluscum contagiosum, dermoid cysts, neurofibroma, neurofibromatosis, schwannoma (neurilemoma), pleiomorphic adenoma |
| Malignant tumors | Basal cell carcinoma, squamous cell carcinoma, mucoepidermoid carcinoma, melanoma, retinoblastoma, embryonal rhabdomyosarcoma, meningioma, adenoid cystic carcinoma, lymphoid tumors of the orbit, mesenchymal tumors (fibrous hystiocytoma) of the orbit, nasopharyngeal carcinoma. |
| Vascular lesions | Hemangioma, lymphangioma |

TABLE XIb

Ophthalmic diseases treatable using compounds described in this invention (cont'd)
Disease Category/Examples of Diseases, Causes or Associated Conditions*

| | |
|---|---|
| Conjunctivitis | Acute allergic conjunctivitis (e.g. drug-related inflammation, hypersensitivity reactions), chronic (vernal) conjunctivitis, contact lens-associated conjunctivitis, e.g. giant papillary conjunctivitis, conjunctival ulceration, including ulceration associated with mucous membrane, conjunctival warts |
| Blepharitis | Inflammatory etiologies, e.g. blepharitis secondary to rosacea |
| Ophthalmic fibrosis | Steven's-Johnson syndrome with progressive fibrosis and scarring, cicatrization and symblepharon. |
| Corneal injury | Corneal abrasion or ulceration (e.g. contact lens-related injury), or corneal injury of any etiology*. |
| Dry eye syndrome | See Table below |
| Pterygium, pinguecula | |
| Pemphigoid | Includes ophthalmic pemhigori |
| Scleritis/ Episcleritis | |
| Iridocyclitis | |
| Endophthalmitis | |
| Uveal tract diseases | Including glaucoma (primary and secondary etiologies) Uveitis, uveoretinitis, panuveitis, all etiologies* |
| Vitreitis, retinitis | e.g. congenital retinitis, retinitis pigmentosa |
| Infectious retinitis | Viral (e.g. herpes, cytomegalovirus, HIV), tuberculous, syphilitic, fungal (e.g. histoplasmosis) |
| Chorio- retinopathies | Chorioretinitis, choroiditis, vitreitis, |
| Retinopathies | e.g. Diabetic retinopathy, hypertensive retinopathy |
| Maculopathies | age-related-macular degeneration, white dot syndromes |
| Cataract | Related to diabetes, age, collagen vascular diseases |
| Ocular palsies | |

*Etiologies of ophthalmic diseases treatable according to the methods of this invention include diseases induced or caused by physical agents (e.g. UV radiation), chemical agents (e.g. acids, caustic solvents) immunological etiologies (e.g. collagen vascular diseases, auto-immune, T lymphocyte-related), infectious agents such as viruses (HSV, CMV, HIV), mycoplasma, tuberculosis, syphilis, fungac (histoplasmosis)

TABLE IXc

Ophthalmic diseases treatable using compounds described in this invention (cont'd) - Etiologies of dry eye syndrome I. Conditions Characterized by Hypofunction of the Lacrimal Gland:

A. Congenital
Familial dysautonomia (Riley-Day syndrome), aplasia of the lacrimal gland (congenital alacrima), trigeminal nerve aplasia, ectodermal dysplasia
B. Acquired
1. Systemic Diseases, e.g. Sjögren's Syndrome, progressive systemic sclerosis, sarcoidosis, leukemia, lymphyoma, amyloidosis, hemochromatosis,
2. Infection, e.g. mumps
3. Injury, e.g. surgical removal of lacrimal gland, irradiation, chemical burn
4. Medications, e.g. antihistamines, antimuscarinics (atropine, scopolamine),
general anesthetics (halothane, nitrous oxide), Ǝ-adrenergic blockers (timolol, practolol), neurogenic, neuroparalytic (facial nerve palsy)

II. Conditions Characterized by Mucin Deficiency

Avitaminosis A, Stevens-Johnson syndrome, ocular pemphigoid, chronic conjuncitivitis (e.g. trachoma), chemical burns, drugs and medications III. Conditions Characterized by Lipid Deficiency Lid margin scarring, blepharitis IV. Defective Spreading of Team Film Caused by the Following:

A. Eyelid abnormalities
1. Defects, colboma
2. Ectropion or entropion
3. Keratinization of lid margin
4. Decreased or absent blinking secondary to: neurologic disorders, hyperthyroidism, contact lens, drugs and medications, herpes simplex keratitis, leprosy, conjunctival abnormalities, pterygium, symblepharon, proptosis

TABLE IXd

Ophthalmic diseases treatable using compounds described in this invention (cont'd) - Non-hereditary and hereditary degenerative diseases

| | |
|---|---|
| Macular disorders: | All etiologies and manifestations, including age-related macular degeneration, exudative macular degeneration, atrophic macular |

TABLE IXd-continued

Ophthalmic diseases treatable using compounds described in this invention (cont'd) - Non-hereditary and hereditary degenerative diseases

| | |
|---|---|
| | degeneration, crystalline retinopathies, retinal toxicosis of systemic medications, idiopathic central serous choroidiopathy, macular edema |
| Retinovascular diseases and retinopathies: | Retinopathy, vasculo-occlusive r., ischemic r., idiopathic r., hypertensive r., proliferative r., diabetic r., vitreoretinopathy, vasculopathies associated with telangiectasias or aneurysms, retinopathies associated with lupus erythematosus, rheumatoid arthritis, multiple sclerosis, myasthenia gravis, uveoretinitis or diabetes mellitus, glaucomatous retinopathies |
| Glaucoma: | All etiologies and manifestations, including primary and secondary open-angle glaucoma, angle-closure glaucoma, glaucoma associated with intraocular inflammation, elevated intraocular pressure associated with acute glaucoma, steroid-induced glaucoma, glaucoma associated with intraocular hemorrhage, pseudoexfoliative syndrome, glaucomatous optic neuropathy and other degenerative changes (e.g. retinopathy) associated with glaucoma |
| Cataract: | All etiologies and manifestations, including age-related (UV radiation) cataract, cataract associated with systemic diseases such as collagen vascular disease, diabetes mellitus, Wilson's disease |
| Other diseases: | Primary or secondary retinal detachment |

TABLE IXe

Ophthalmic diseases treatable using compounds described in this invention (cont'd) - Congenital degenerative retinopathies I. Primary pigmented retinopathies, all gene types Autosomal dominant retinitis pigmentosa, e.g. rod-cone and cone-rod degenerations
Autosomal recessive retinitis pigmentosa, e.g. rod-cone and cone-rod degenerations,
Lerner's amaurosis congenita
X-linked recessive pigmented retinopathies, e.g. choroideremia
2. Secondary pigmented retinopathies (retinopathies associated with systemic diseases)

Autosomal dominant pigmented retinopathies, e.g. Paget's disease, Charcot-Marie-Tooth, disease, Steinert's disease, Pierre-Marie syndrome
Autosomal recessive pigmented retinopathies, e.g. diabetes mellitus, mannosidoses, mucopolysccharidoses, Batten's d., Refsum's d., Usher syndrome
X-linked recessive pigmented retinopathies, e.g. Hunter syndrome

TABLE X

Diseases or conditions treatable using compounds described in this invention

I. Promote healing in the following clinical situations:

Surgical or traumatic wounds to healthy tissues or organs
Wounds caused by chemical or physical agents, e.g. ulcers caused by caustic or erosive chemicals, pressure sores, etc.

TABLE X-continued

Diseases or conditions treatable using compounds described in this invention

Wounds associated with disease states, e.g. diabetic ulcers etc.
Wounds in diseased tissues or organs
II. Promote cell survival and prevent apoptosis in neurodegenerative diseases:

Alzheimer's disease
Parkinson's disease
Amyotrophic lateral sclerosis
Spinal cord ischemia, injury or transection secondary to trauma or disease
III. Attenuation or arrest of the following conditions or processes:

The natural aging of cells and tissues
Aging induced by chemical or physical agents, e.g. sun-induced skin aging
Accelerated aging associated with diseases, e.g. Werner's syndrome
IV. Vitalization and revitalization of organs and tissues Promoting cell growth and preventing cell death in the aging process
Promoting therapeutic or non-pathological angiogenesis as a therapeutic approach to treating diseases such as congestive heart failure and cardiomyopathy
Promoting growth of organs and tissues for repair or transplantation The oral route of administration is the preferred mode for treatment or prevention of type 2 diabetes, the metabolic syndrome, and most other chronic disorders. Therapeutic agents of the invention are usually delivered or administered topically for treating disorders involving the eye or the skin except in some cases where oral administration is the preferred mode. Additionally, the agents can be delivered parenterally, especially for treatment of retinitis and degenerative retinal diseases, and for other conditions in Tables I through X, that do not respond to oral or topical therapy, or for conditions where oral or topical therapy is not feasible. Parenteral therapy is typically oral, intraocular, transcutaneous, intradermal, intrathecal, intramuscular, intra-articular, by inhalation, intravascular, sublingual, by suppository (e.g. per-rectum or vaginal application), by inhalation, or other parenteral route.

A preferred way to practice the invention for dermatological or ophthalmic disorders in Tables I through X to which this method is applicable, is to apply the compound of interest, in a cream, lotion, ointment, or oil based carrier, directly to the lesion. Typically, the concentration of therapeutic compound in a cream, lotion, or oil is 0.1 to 2.5%. In general, the preferred route of administration is oral, topical, intraocular or parenteral. Topical administration is preferred in treatment of lesions of the skin as in psoriasis, external eye as in conjunctivitis, keratitis, scleritis, squamous cell carcinoma, corneal erosion, dry eye syndrome, and anterior compartment of the eye as in glaucoma, uveitis and other diseases of the uveal tract, where such direct application is practical and clinically indicated.

Oral administration is a preferred alternative for treatment of other lesions discussed in Tables I through X, where direct topical application is not useful as in the treatment of chronic or acute systemic diseases, and diseases of the posterior segment of the eye, as in retinitis and other retinal degenerative diseases. Intravascular (intravenous being the preferred route) administration may be necessary in disorders that cannot be effectively treated by topical or oral administration.

Intraocular, transcutaneous, intradermal, intrathecal, intramuscular, intra-articular injections or other invasive technique are preferred alternative in cases where the practitioner wishes to treat one or a few specific areas or lesions depending on their location within the eye. Usually, the compound is delivered in an aqueous solution. Additionally, the therapeutic compounds are injected directly into lesions (intra-lesion administration) in appropriate cases. Intradermal administration is an alternative for extraocular lesions. Intra-lesional and intradermal injections are alternative routes of application for certain lesions, e.g. extraocular neoplastic or hyperplastic lesions such as squamous cell carcinoma and condyloma, respectively. Inhalation therapy is preferred for pulmonary diseases, sublingual and intra-rectal suppository is preferred for rapid delivery or in clinical situations where delivery via the oral or intravascular route is inconvenient or problematic. Application via vaginal topical formulation or via suppository formulation is preferred for diseases localized to the vagina or other segment of the urogenital tract.

An effective quantity of the compound of interest is employed in treatment. The dosage of compounds used in accordance with the invention varies depending on the compound and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular compound. The dose should be sufficient to ameliorate symptoms or signs of the disease treated without producing unacceptable toxicity to the patient.

In general, an effective amount of the compound is that which provides either subjective relief of symptoms or an objectively identifiable improvement as noted by the clinician or other qualified observer. A typical oral dose is between 1 mg per day up to 1000 mg per day according to the judgment of the clinician. Typically, the dosage per day of the compounds of this invention will depend on the their ability to activate PPARgamma and their ability to block the angiotensin II type 1 receptor. The dosages of these compounds will generally run between 0.1 mg to 1000 mg per day with a common dose being 5 mg per day to 300 mg per day. Typically, the greater the ability to activate PPARgamma and to block the angiotensin II receptor, the more effective the compound, and the lower the dosage that is an effective amount.

An oral dosing schedule is typically, a single dose once a day. However, more than one dose can be given per day. Because of the lower incidence of undesirable side effects, the compounds of this invention can be given until improvement in the disorder of interest is observed and continued as necessary to maintain such an improved clinical state. The compounds may or may not be administered with food or with other agents depending on how food or other agents affects their absorption by the body and depending on the judgment of those skilled in the therapeutic art.

The dosage can be administered once or twice a day, but the clinician can recommend more or less frequent dosing. Once a therapeutic result is achieved, the compound can be tapered or discontinued or continued according to the recommendation of the clinician. Occasionally, side effects warrant discontinuation of therapy.

An effective quantity of the compound of interest is employed in treatment. The dosage of compounds used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

Broadly, an oral dosing schedule is from about 0.1 mg to about 1000 mg once or twice a day. Using telmisartan as the prototype agent for the purpose of this invention, a convenient oral dose for an adult patient is approximately 80 mg to 160 mg per day but could be less or more depending on the indication. A dosage range for topical treatment is about 0.1% to about 1% (weight/volume) in a gel, cream or ointment, applied twice a day. A usual dose for intramuscular or intraocular injection is 0.25 to 2.5 mg, depending on the compartment of the eye to be treated and on the lean body mass of the patient. A typical dosage for intra-dermal administration is about 2.5 to 25 mg per injection per site. A typical dosage for intravenous or intramuscular administration in an adult patient would be between 50 and 250 mg per day given in single or divided doses depending on the judgment of the practitioner.

Compounds and Formulations of the Invention

Compounds useful for the application of methods described in this invention include all existing synthetic and naturally occurring agents that both increase the activity of PPARgamma and block or antagonize the activity of the angiotensin II type 1 receptor as well as those yet to be discovered that have such dual ability. Preferred compounds for the purposes of this invention include telmisartan (Micardis®), irbesartan (Avapro®) as well as any derivatives or formulations thereof and any new ARBs that may be marketed in the future that have the ability to activate PPAR-gamma.

For oral administration, either solid or fluid unit dosage forms can be prepared. For preparing solid compositions such as tablets, the compound of interest is mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound of interest with an inert pharmaceutical diluent and filling the mixture into a hard gelatin capsule of appropriate size. Soft gelatin capsules are prepared by machine encapsulation of a slurry of the compound of interest with an acceptable vegetable oil, light liquid petrolatum or other inert oil. Fluid unit dosage forms for oral administration such as syrups, elixirs and suspensions can be prepared. The water-soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Appropriate formulations for parenteral use are apparent to the practitioner of ordinary skill. Usually, the therapeutic compound is prepared in an aqueous solution (discussed below) in a concentration of from about 1 to about 100 mg/ml. More typically, the concentration is from about 10 to 60 mg/ml or about 20 mg/ml. Concentrations below 1 mg/ml may be necessary in some cases depending on the solubility and potency of the compound selected for use. The formulation, which is sterile, is suitable for various topical or parenteral routes including sublingual, by suppository (e.g. per-rectum or vaginal application), oral, intravascular, intradermal, by inhalation, intramuscular, intra-articular, intravenous, or other parenteral route.

In addition to the therapeutic compound, the compositions may include, depending on the formulation and mode of delivery desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline, organic or inorganic salt solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include cosolvents, surfactants, oils, humectants, emollients, preservatives, stabilizers and antioxidants. Any pharmacologically acceptable buffer may be used, e.g., tris or phosphate buffers. Effective amounts of diluents, additives and excipients are those amounts which are effective to obtain a pharmaceutically acceptable formulation in terms of solubility, biological activity, etc.

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals. Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention includes a therapeutic compound which may be formulated with conventional, pharmaceutically acceptable, vehicles for topical, oral or parenteral administration. Formulations may also include small amounts of adjuvants such as buffers and preservatives to maintain isotonicity, physiological and pH stability. Means of preparation, formulation and administration are known to those of skill. See generally Remington's Pharmaceutical Science 15th ed., Mack Publishing Co., Easton, Pa. (1980).

To prepare a topical formulation for the treatment of ophthalmological or dermatological or other disorders listed in Tables I through X, a therapeutically effective concentration of the compound is placed in a dermatological vehicle as is known in the art. The amount of the therapeutic compound to be administered and the compound's concentration in the topical formulations depend upon the vehicle, delivery system or device selected, the clinical condition of the patient, the side effects and the stability of the compound in the formulation. Thus, the physician employs the appropriate preparation containing the appropriate concentration of the therapeutic compound and selects the amount of formulation administered, depending upon clinical experience with the patient in question or with similar patients.

The therapeutic compound is optionally administered topically by the use of a transdermal therapeutic system (see Barry, Dermatological Formulations, (1983) p. 181 and literature cited therein). While such topical delivery systems have been designed largely for transdermal administration of low molecular weight drugs, by definition they are capable of percutaneous delivery. They may be readily adapted to administration of the therapeutic compounds of the invention by appropriate selection of the rate-controlling microporous membrane.

For ophthalmic applications the therapeutic compound is formulated into solutions, suspensions, and ointments appropriate for use in the eye. The concentrations are usually as discussed above for topico-local preparations. For ophthalmic formulations, see Mitra (ed.), Ophthalmic Drug Delivery Systems, Marcel Dekker, Inc., New York, N.Y. (1993) and also Havener, W. H., Ophthalmic Pharmacology, C. V. Mosby Co., St. Louis (1983).

The concentration of the therapeutic compound used depends on the mode of delivery. For topical ophthalmic and extraocular formulations, the concentration of the therapeutic compound is in the range of about 0.01% weight/weight (w/w) to about 10% w/w. Typically, the concentration of the therapeutic compound for this mode of delivery is in the range of about 0.025% w/w to about 2.5% w/w. Solid dispersions of the therapeutic compound as well as solubilized preparations can be used. For intraocular formulations (chemical delivery or delivery by invasive device), the therapeutic compound is delivered at a concentration high enough to achieve a final concentration in the range of about 0.1:mol/L to about 10:mol/L within the target ophthalmic compartment (e.g. the posterior chamber for the treatment of retinal diseases). Typically, for this mode of delivery, the final concentration of the therapeutic compound is in the range of about 0.25:mol/L to about 5:mol/L. Solid dispersions of the therapeutic compound as well as solubilized preparations can be used. Thus, the precise concentration is subject to modest but not undue experimental manipulation well within the skill of the ordinary medical practitioner in order to optimize the therapeutic response. Suitable vehicles include oil-in-water or water-in-oil emulsions for preparation of ointments using mineral oils, petrolatum, lanolin, glycerin and the like as well as gels such as hydrogel. A preferred embodiment of the present invention involves administration of semi-solid or solid implants containing PPARgamma agonists.

Slow or extended-release delivery systems, including any of a number of biopolymers (biological-based systems), systems employing liposomes, colloids, resins, and other polymeric delivery systems or compartmentalized reservoirs, can be utilized with the compositions described herein to provide a continuous or long term source of therapeutic compound. Such slow release systems are applicable to formulations for delivery via topical, intraocular, oral, and parenteral routes.

As mentioned above, delivery intravascularly, intra-articularly, intramuscularly, intra-articularly, intradermally, or other parenteral route can be accomplished by injection, cannula or other invasive device designed to introduce precisely metered amounts of a desired formulation to a particular compartment or tissue. For example, delivery to certain areas within the eye, in situ, can be accomplished by injection, cannula or other invasive device designed to introduce precisely metered amounts directly or contained in a reservoir for slow release in situ, of a desired formulation to a particular compartment or tissue within the eye (e.g. anterior or posterior chamber, uvea or retina). Preferably, a solid or semisolid implant can be delivered subretinally using the instrumentation and methods described in U.S. Pat. No. 5,817,075 and U.S. Pat. No. 5,868,728.

Combination Use of Drugs

A compound according to the present invention may be used in combination with a diabetes mellitus-treating agent, a diabetic complication-treating agent, an antihyperlipemic agent, a hypotensive or antihypertensive agent, an antiobesity agent, a diuretic, a chemotherapeutic agent, an immunotherapeutic agent, and immunosuppressive agent, and the like (hereinafter referred to as a concomitant agent). In such case, the periods of the treatments with a compound according to the present invention and with a concomitant agent are not limited particularly, and such agents may given to a patient simultaneously or at a certain time interval. The dose of a concomitant drug may appropriately be determined based on the customary clinical dose. The ratio between a compound according to the present invention and a concomitant agent may be appropriately determined based on various factors such as the subject to be treated, the administration route, the disease or the condition to be treated and the combination of the drugs. For example, when a human is treated, 1 parts by weight of a compound according to the present invention is combined with 0.01 to 100 parts by weight of a concomitant agent.

Examples of an agent for treating diabetes mellitus are an insulin formulation (e.g., animal insulin formulations extracted from a pancreas of a cattle or a swine; a human insulin formulation synthesized by a gene engineering technology using microorganisms or methods), an insulin sensitivity enhancing agent (e.g., pioglitazone hydrochloride, troglitazone, rosiglitazone and the like), an alpha-glycosidase inhibitor (e.g., voglibose, acarbose, miglitol, emiglitate and the like), a biguanide (e.g., phenformin, metformin, buformin and the like), or a sulfonylurea (e.g., tolbutamide, glibenclamide, gliclazide, chlorpropamide, tolazamide, acetohexamide, glyclopyramide, glimepiride and the like) as well as other insulin secretion-promoting agents (e.g., repaglinide, senaglinide, nateglinide, mitiglinide, GLP-1 and the like), amyrin agonist (e.g. pramlintide and the like), phosphotyrosinphosphatase inhibitor (e.g. vanadic acid and the like) and the like.

Examples of an agent for treating diabetic complications are an aldose reductase inhibitor (e.g., tolrestat, epalrestat, zenarestat, zopolrestat, minalrestat, fidareatat, SK-860, CT-112 and the like), a neurotrophic factor (e.g., NGF, NT-3, BDNF and the like), PKC inhibitor (e.g. LY-333531 and the like), AGE inhibitor (e.g. ALT946, pimagedine, pyradoxamine, phenacylthiazolium bromide (ALT766) and the like), an active oxygen quenching agent (e.g., thioctic acid or derivative thereof, a bioflavonoid including flavones, isoflavones, flavonones, procyanidins, anthocyanidins, pycnogenol, lutein, lycopene, vitamins E, coenzymes Q, and the like), a cerebrovascular dilating agent (e.g., tiapride, mexiletene and the like).

An antihyperlipemic agent may for example be a statin-based compounds which is a cholesterol synthesis inhibitor (e.g., pravastatin, simvastatin, lovastatin, atorvastatin, fluvastatin, rosuvastatin and the like), a squalene synthetase inhibitor or a fibrate compound having a triglyceride-lowering effect (e.g., gemfibrozil, bezafibrate, clofibrate, sinfibrate, clinofibrate and the like).

A hypotensive agent may for example be an angiotensin converting enzyme inhibitor (e.g., captopril, enalapril, delapril, benazepril, cilazapril, enalapril, enalaprilat, fosinopril, lisinopril, moexipril, perindopril, quinapril, ramipril, trandolapril, and the like) or an angiotensin II antagonist (e.g., losartan, candesartan cilexetil, eprosartan, valsartan, telmisartan, irbesartan, tasosartan and the like).

An antiobesity agent may for example be a central antiobesity agent (e.g., dexfenfluramine, fenfluramine, phentermine, sibutramine, amfepramone, dexamphetamine, mazindol, phenylpropanolamine, clobenzorex and the like), a pancreatic lipase inhibitor (e.g., orlistat and the like), β-3 agonist (e.g., CL-316243, SR-58611-A, UL-TG-307, SB-226552, AJ-9677, BMS-196085 and the like), a peptide-based appetite-suppressing agent (e.g., leptin, CNTF and the like), a cholecystokinin agonist (e.g., lintitript, FPL-15849 and the like) and the like.

A diuretic may for example be a xanthine derivative (e.g., theobromine sodium salicylate, theobromine calcium salicylate and the like), a thiazide formulation (e.g., ethiazide, cyclopenthiazide, trichloromethiazide, hydrochlorothiazide, hydroflumethiazide, bentylhydrochlorothiazide, penflutizide, polythiazide, methyclothiazide and the like), anti-aldosterone formulation (e.g., spironolactone, triamterene and the like), a decarboxylase inhibitor (e.g., acetazolamide and the like), a chlorbenzenesulfonamide formulation (e.g., chlorthalidone, mefruside, indapamide and the like), azosemide, isosorbide, ethacrynic acid, piretanide, bumetanide, furosemide and the like.

A chemotherapeutic agent may for example be an alkylating agent (e.g., cyclophosphamide, iphosphamide and the like), a metabolism antagonist (e.g., methotrexate, 5-fluorouracil and the like), an anticancer antibiotic (e.g., mitomycin, adriamycin and the like), a vegetable-derived anticancer agent (e.g., vincristine, vindesine, taxol and the like), cisplatin, carboplatin, etoposide and the like. Among these substances, 5-fluorouracil derivatives such as furtulon and neofurtulon are preferred.

An immunotherapeutic agent may for example be a microorganism or bacterial component (e.g., muramyl dipeptide derivative, picibanil and the like), a polysaccharide having immune potentiating activity (e.g., lentinan, sizofilan, krestin and the like), a cytokine obtained by a gene engineering technology (e.g., interferon, interleukin (IL) and the like), a colony stimulating factor (e.g., granulocyte colony stimulating factor, erythropoetin and the like) and the like, among these substances, those preferred are IL-1, IL-2, IL-12 and the like.

An immunosuppressive agent may for example be a calcineurin inhibitor/immunophilin modulator such as cyclosporine (Sandimmune, Gengraf, Neoral), tacrolimus (Prograf, FK506), ASM 981, sirolimus (RAPA, rapamycin, Rapamune), or its derivative SDZ-RAD, a glucocorticoid (prednisone, prednisolone, methylprednisolone, dexamethasone and the like), a purine synthesis inhibitor (mycophenolate mofetil, MMF, CellCept(R), azathioprine, cyclophosphamide), an interleukin antagonist (basiliximab, daclizumab, deoxyspergualin), a lymphocyte-depleting agent such as antithymocyte globulin (Thymoglobulin, Lymphoglobuline), anti-CD3 antibody (OKT3), and the like.

In addition, an agent whose cachexia improving effect has been established in an animal model or at a clinical stage, such as a cyclooxygenase inhibitor (e.g., indomethacin and the like) [Cancer Research, Vol.49, page 5935-5939, 1989], a progesterone derivative (e.g., megestrol acetate) [Journal of Clinical Oncology, Vol.12, page 213-225, 1994], a glucosteroid (e.g., dexamethasone and the like), a metoclopramide-based agent, a tetrahydrocannabinol-based agent (supra), a lipid metabolism improving agent (e.g., eicosapentanoic acid and the like) [British Journal of Cancer, Vol.68, page 314-318, 1993], a growth hormone, IGF-1, or an antibody against TNF-.alpha., LIF, IL-6, oncostatin M which are cachexia-inducing factors may also be employed concomitantly with a compound according to the present invention.

The possible preferred combinations of the agents for the prevention and/or treatment of diabetes are, a PPARgamma activator with ARB activity, and:
1) an insulin formulation and a biguanide;
2) a sulfonylurea agent and a biguanide;
3) a sulfonylurea agent and an alpha-glycosidase inhibitor;
4) a biguanide and an alpha-glycosidase inhibitor;
5) a blood sugar reducing agent and the other kind of agents for treating diabetic complications;
6) an 3-hydroxy-3-methylglutaryl coenzyme A (HMG CoA) reductase inhibitor;
7) any other two kinds of agents mentioned above.
8) an agent that inhibits activity of angiotensin converting enzyme Incase that the compound or the composition of the present invention is used in combination with the other agent, an amount of each other agent can be reduced in a range which is safe in light of its adverse effect. Especially, an insulin sensitivity enhancing agent, a biguanide and a sulfonylurea agent can be used in less dose than regular dose so that adverse effects which may be caused by these agents can be safely avoided. In addition, an agent for treating diabetic complications, an antihyperlipemic agent and a hypotensive agent can also be used in less dose, so that adverse effect which may be caused by them can be avoided effectively.

As noted above, by administering both an ARB and a PPAR activator formulated together in a single pill or tablet, one can also treat glucose intolerance or type 2 diabetes and other PPAR responsive disorders without causing fluid retention, edema, or congestive heart failure. For this purpose, one can prepare and use a pharmaceutical composition comprising: (i) a PPAR activator in a therapeutically effective amount sufficient to prophylactically prevent, slow, delay or treat a metabolic, inflammatory, atopic, autoimmune, proliferative, or cardiovascular disorder in humans; (ii) an angiotensin II type 1 receptor antagonist in a therapeutically effective amount sufficient to prevent, slow, delay, or treat fluid retention, peripheral edema, pulmonary edema, or congestive heart failure; and (iii) a pharmaceutically acceptable carrier. For this purpose, the PPAR activator in the pharmaceutical composition can be is a thiazolidinedione selected from the group of compounds consisting of rosiglitazone, pioglitazone, KRP 297, MCC-555, netoglitazone, rivoglitazone and balagitazone, or an analog thereof, or a tautomeric form thereof, or a pharmaceutically acceptable salt thereof, or a pharmaceutically acceptable solvate thereof. Alternatively, the PPAR activator in the pharmaceutical composition can be a non-thiazolidinedione selected from the group of compounds consisting of tesaglitazar, farglitazar, ragaglitazar, LY818, T131, LSN862, DRF 4832, LM 4156, LY 510929, LY 519818, TY 51501, X 334, or an analog thereof, or a tautomeric form thereof, or a pharmaceutically acceptable salt thereof, or a pharmaceutically acceptable solvate thereof. Other thiazolidinedione or non-thiazolidinedione activators of PPARs that are familiar to those skilled in the art can also be employed. For purposes of making the pharmaceutical composition, the angiotensin II type 1 receptor antagonist can be a compound selected from the group consisting of telmisartan, irbesartan, valsartan, losartan, candesartan, candesartan cilexetil, olmesartan, olmesartan medoximil, losartan, valsartan, eprosartan, irbesartan, tasosartan, pomisartan, ripisartan, and forasartan, or an analog thereof, or a tautomeric form thereof, or a pharmaceutically acceptable salt thereof, or a pharmaceutically acceptable solvate thereof.

The compounds in this invention can also be given orally in combination with natural or synthetic compounds that bind to or modify the activity of the vitamin D receptor or other nuclear hormone receptor or in combination with compounds that bind to or modify the activity of the retinoid X receptor to provide for a synergistic effect in the treatment or prevention of the disorders listed in Tables I through X. Examples of such compounds that provide for synergistic effect when given in combination with the drugs encompassed by the current invention include vitamin D analogs, various retinoic acid derivatives, and other ligands for retinoid X receptors or retinoic acid receptors including but not limited to compounds such as LG100268, tazarotene, TTNPB, AGN 190121, adapalene or LGD1069 (Targretin). Synergistic therapeutic effects can be achieved by oral or topical administration of the drugs encompassed in the current invention together with orally, topically or intravenously administered drugs that bind to and modify the activity of either the vitamin D receptor, the glucocorticoid receptor, the intracellular enzyme calcineurin, the retinoid X receptors, the retinoic acid receptors, or other PPARs such as PPARalpha or PPARdelta. A preferred dosage range for administration of a retinoic acid derivative or retinoid would typically be from 0.1 to 100 mg per square-meter of body surface area, depending on the drug's ability to bind to or modify the activity of its cognate nuclear receptor, given in single or divided doses, orally or by continuous infusion, two or three times per day. For synergistic therapy, the preferred dosages and routes and frequency of administration of the vitamin D analogs or retinoid compounds can be similar to the dosages and routes and frequency of administration ordinarily recommended for these agents when given without PPAR activators. Examples of effective retinoids are 9-cis-retinoic acid, 13-cis-retinoic acid, all-trans-retinoic acid (at-RA). Preferred retinoids for this purpose would include 13-cis-retinoic acid, tazarotene, or Targretin. A preferred dosage range for systemic administration of a vitamin D analog would typically be from 0.1 to 100 mg per square-meter of body surface area, depending on the drug's ability to bind to and or activate its cognate vitamin D receptor, given in single or divided doses, orally or by continuous infusion, two or three times per day. Examples of effective vitamin D analogs are 1,25-dihydroxy-vitamin D, calcipotriene and calcipotriol. The dosage range and routes and frequency of administration of PPAR activators required to achieve synergistic effects when given with vitamin D or retinoid derivatives are the same as those described elsewhere in this disclosure. The preferred mode of administration of these drugs for synergistic therapeutic purposes would be orally although alternatively one can use topical or parenteral routes of administration. The dosages and the modes and frequency of administration of the vitamin D or retinoid related compounds for synergistic topical therapy would be similar to those ordinarily recommended for these agents when given without PPAR activators. The dosage range and the modes and frequency required for topical administration of the flavonoid thiazolidine derivatives given in combination with vitamin D or retinoid related compounds are the same as those described elsewhere in this disclosure.

Synergistic therapeutic effects can be achieved by oral or topical administration of the drugs encompassed in the current invention together with orally, topically or intravenously administered natural or synthetic antioxidants. These include ascorbic acid and its derivatives (e.g. vitamin C), the tocopherols (e.g. vitamin E, vitamin E succinate), carotenes and carotenoids (e.g. β-carotene), alpha-lipoic acid, probucols, flavones, isoflavones and flavonols (e.g. quercetin, genistein, catechin, apigenin, lutein, luteolin), lycopene, pycnogenol, glutathione and its derivatives (e.g. N-acetyl-cysteine and dithiothreitol), and phytoestrogens and phenolic anthocyanidin and procyanidin derivatives (e.g. resveratrol, cyanidin, cinnamic acid).

The compounds of the instant invention are further useful to suppress the mediators of neurogenic inflammation (e.g. substance P or the tachykinins), and may be used in the treatment of rheumatoid arthritis; psoriasis; topical inflammation such as is associated with sunburn, eczema, or other sources of itching; and allergies, including asthma. The compounds can also function as neuromodulators in the central nervous system, with useful applications in the treatment of Alzheimer's disease and other forms of dementia, pain (as a spinal analgesic), and headaches. Furthermore, in disorders involving myocardial fibrosis, myocardial ischemia, pathological conditions secondary to the autoimmune response to allograft transplantation, the splanchnic blood flow, including hepatic fibrosis, cirrhosis and esophageal varices, the compounds of the invention can provide cytoprotection.

The present invention is further detailed in the following Examples and Methods which are not intended to restrict the present invention.

Method for Designing and Identifying an ARB as a PPAR Ligand

ARBs, or derivatives thereof, may be tested for their ability to activate the various PPAR isoforms by utilizing standard screening methods known to those skilled in the art including but not limited to cell based transactivation assays or cell free assays that test the ability of a compound to activate a PPAR construct by measuring the output of a reporter signal that reflects the extent of the PPAR activation. For example, the angiotensin receptor blocker telmisartan is added to the culture media of CV1 cells or other cells that can be transfected with a full length or partial PPAR cDNA sequence together with a reporter construct containing a PPAR response element or other appropriate response element fused to a reporter gene such as luciferase. The ability of telmisartan to activate PPARgamma is tested by measuring the luciferase reporter gene activity and it is found that telmisartan causes a significant increase in reporter gene activity well above the background level present in the cells not treated with telmisartan. Similar experiments are performed with irbesartan which is also found to activate PPARgamma. Any ARBs found to activate PPARgamma according to these or other methods can be used to treat disorders known to be responsive to PPAR activators.

One can also make chemical modifications to existing ARBs that can be predicted to enhance their ability to activate PPARgamma. Therefore, one can design ARBs that are particularly effective in treating disorders known to be responsive to PPAR activators without causing fluid retention, edema, or congestive heart failure. One can also modify chemical structures of PPAR activators to enhance their ability to inhibit ACE activity or block angiotensin receptors. This can be accomplished using published information on the crystal structures of the PPARs and published information on the amino acid residues and regions of the PPARs that are important in receptor activation together with known methods for testing ability of compounds to inhibit ACE activity or block angiotensin receptors. Using methods known to those skilled in the art, one can make chemical modifications to existing ARBs or ACE inhibitors or design derivatives thereof that can be predicted to have improved ability to activate PPARs than existing ARBs or ACE inhibitors.

Method of Identifying a PPAR Ligand with Decreased Risk for Causing Fluid Retention, Edema, or Congestive Heart Failure One can identify PPARgamma activators that have improved safety profile and decreased risk for causing fluid retention, edema, or congestive heart failure by testing their ability to inhibit angiotensin converting enzyme activity or their ability to block the angiotensin receptor. PPARgamma ligands or PPARgamma activators that also inhibit ACE activity or block angiotensin II type 1 receptors represent an improvement over existing PPAR ligands for treating PPAR responsive disorders because they have reduced likelihood of causing fluid retention, edema, or congestive heart failure. A variety of assays are available that can be used by those skilled in the art to determine whether a PPARgamma activator can also block the angiotensin II type 1 receptor or inhibit the activity of angiotensin converting enzyme. According to the method of Groff J L, et al. (Simplified enzymatic assay of angiotensin-converting enzyme in serum. Clin Chem. 1993; 39:400-4) or other assays that are familiar to those skilled in the art of testing compounds for their ability to inhibit angiotensin converting enzyme activity.

The ability of a PPAR ligand to selectively block the interaction of angiotensin II (AII) with the angiotensin II type 1 receptor can be determined by the method of competitive binding of radiolabelled angiotensin II to preparations enriched in the AII type 1 receptor vs. the AII type 2 receptor. Other methods that are familiar to those skilled in the art of identifying compounds that block the angiotensin II type 1 receptor can also be used to determine whether a PPAR activator can block the angiotensin II type 1 receptor to any degree which would be useful in identifying a PPAR activator that is unlikely to cause fluid retention, edema, or congestive heart failure.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all and only experiments performed. Efforts have been made to ensure accuracy with respect to numbers used (e.g. amounts, temperature, etc.) but some experimental errors and deviations should be accounted for. Unless indicated otherwise, parts are parts by weight, molecular. weight is weight average molecular weight, temperature is in degrees Celsius, and pressure is at or near atmospheric.

Example 1

Identification of Angiotensin II Type 1 Receptor Blockers that Activate PPARGamma PPARγ activity was determined by transactivation assays in CV-1 cells (CCL-70 line from ATCC, Bethesda, Md.) transfected using the GenePorter transfection reagent (Gene Therapy Systems, San Diego, Calif.) to deliver 200 ng of a PPARγ expression plasmid and 1 μg of a luciferase reporter plasmid and 400 ng pCMVSport β-gal (Gibco, Grand Island, N.J.) as an internal control 24 hr post-transfection, cells were treated with varying concentrations of the test compounds (telmisartan, irbesartan, valsartan, losartan, the active metabolite of losartan, the active forms of candesartan and olmesartan, rosiglitazone, or pioglitazone) and incubated for an additional 24 hr. Cell extracts were assayed for luciferase and β-galactosidase activity using Promega (Madison, Wis.) assay systems. All treatments were performed in triplicate, and normalized for β-galactosidase activity. Agonist concentrations yielding half maximal activation ($EC_{50}$ values) were calculated using GraphPad Prism version 3.03 (GraphPad Software, Inc., San Diego, Calif.).

Telmisartan significantly activated PPARγ (5-8 fold) when tested at concentrations (1-5 μM) that can be achieved in plasma with conventional oral dosing [Stangier, 2000 #14424]. Telmisartan functioned as a moderately potent ($EC_{50}$=5.6 μM), PPARγ agonist, activating the receptor to 25%-30% of the maximum level of activity achieved by the full agonists pioglitazone and rosiglitazone. Irbesartan activated PPARγ (2-3 fold activation) when tested at 10 μM. None of the other ARBs tested caused any significant activation of PPAR even when tested at higher concentrations (more than 10 μM). These experiments demonstrate that two known angiotensin receptor blockers, telmisartan and irbesartan, are also activators of PPARgamma. Because PPARgamma activators can be used to treat and prevent type 2 diabetes, the metabolic syndrome, and other clinical disorders responsive to treatment with PPAR activators, these experiments demonstrate the utility of telmisartan and irbesartan for the prevention and treatment of type 2 diabetes, the metabolic syndrome, and other disorders known to be responsive to treatment with PPAR activators.

Example 2

Measurement of in Vitro Adipocyte Differentiation Activity

The following examples 2 and 3 provide a generic means to measure adipocyte differentation to determine if one has an insulin-sensitizing agent. A mouse preadipocyte cell line (3T3-L1) obtained from the American Type Culture Collection, and the cells are grown in a Dulbecco's modified Eagle medium (DMEM) containing 4.5 g/L glucose, 50 mg/L streptomycin sulfate, 100,000 units/L penicillin-G, 0.584 g/L L-glutamine, 4 mg/L pantothenate, 8 mg/L D-biotin, and 10 mM HEPES (pH 7.2)] supplemented with 10% fetal bovine serum (FBS). The cells are then plated at $1.5 \times 10^4/cm^2$ in a 96-well tissue culture plate (view plate, 96 white, Packard) coated with type 1 collagen. After the cells had reached confluence, the cells were further cultured with differentiation medium DMEM supplemented with 5% FBS, 100 ng/mL insulin, 0.1 mM isobutylmethylxanthine (IBMX), and 1 mM dexamethasone, and containing various concentrations of compounds for 4 days. The compounds added from a stock solution of dimethyl sulfoxide (DMSO). The final concentration of DMSO in the differentiation medium does not exceed 0.1% (v/v). DMSO (0.1%) was added to the control cultures. The medium was replaced with maintenance medium (DMEM supplemented with 5% of FBS and 100 ng/mL of insulin), and the cells cultured for 2 more days. Activity of stimulation of adipogenesis was determined by exposure of the cells to [14-C]-acetic acid (7.4 kBq/mL), and uptake of [14-C]-acetic acid monitored after 1 h of incubation. The medium is discarded and the cells washed twice with phosphate-buffered saline. The cells are air-dried, and 200 mL of scintillation cocktail (Microscint-20, Packard) added to the wells, and counted with a Packard TopCount microplate scintillation counter. Stimulation of adipogenesis is expressed as concentrations equivalent to the [14-C] label uptake counts in the treatment with 10 uM telmisartan.

Example 3

Measurement of in Vivo Insulin-Sensitivity Activity

The hypoglycemic activity of the test compounds in insulin resistant obese fatty (fa/fa) Zucker rats (Jackson Laboratory, Bar Harbor, Me.). These rats are profoundly insulin resistant with extremely high blood concentrations of insulin. Lean littermates (−/−) are used as controls. Each test compounds is administered to three Zucker rats at 10 mg/kg daily for five days after which blood samples are taken in the non-fasting state. Blood samples are collected, placed in a hematocrit centrifuge tube, and centrifuged to obtain plasma. Insulin in the collected plasma is measured by means of a radioimmunoassay kit (Linco Research, Inc, St Charles, Mo.). The insulin-sensitizing activity of the test compounds are calculated as follows:

Insulin-sensitivity activity (%)=[(PI in C−PI in T)/PI in C]×100 where "PI in C" is plasma insulin in control rats and "PI in T" is plasma insulin in rats treated with test compounds.

Example 4

A Clinical Trial Using a PPARgamma Activator to Treat Type 2 Diabetes without Causing Fluid Retention, Edema, or Heart Failure A 49 year old female with hypertension, hypertriglyceridemia, and type 2 diabetes was selected for therapy. Before administration of telmisartan, the patient had a blood pressure of 160/90 mmHg, fasting serum glucose of 183 mg/dl, a fasting serum triglyceride level of 264 mg/dl, and an HDL cholesterol level of 48 mg/dl. The patient is taking another medication for type 2 diabetes but the dose of this medication is held constant throughout the trial. The patient is given telmisartan (Micardis®) at an oral dose of 80 mg/day. After three weeks of telmisartan therapy, the blood pressure is reduced to 143/91 mmHg with little or no improvement in fasting glucose (188 mg/dl), triglyceride (281 mg/dl), or HDL cholesterol levels (50 mg/dl). The oral dose of telmisartan (Micardis®) is then increased to 160 mg/day. After seven weeks of telmisartan (Micardis®) therapy at 160 mg/day, the patient's blood pressure is reduced to 131/81 mmHg and there is a significant improvement in the diabetes with the glucose level reduced to 145 mg/dl, the triglyceride level reduced to 178 mg/dl, and the HDL cholesterol increased to 60 mg/dl. Clinical examination reveals no evidence of any increase in fluid retention, peripheral edema, pulmonary edema, or congestive heart failure. The telmisartan (Micardis®) therapy is continued according to the judgment of the clinician in order to maintain the improved control of the patient's blood pressure and her type 2 diabetes.

Example 5

A Clinical Trial Using a PPARgamma Activator to Treat the Metabolic Syndrome without Causing Fluid Retention, Edema, or Heart Failure A 59 year old female with the metabolic syndrome was selected for therapy. Before administration of telmisartan, the patient had a blood pressure of 160/79 mmHg, fasting serum glucose of 118 mg/dl, fasting insulin level of 15 microunits/ml, fasting triglycerides of 129 mg/dl, and waist girth of 120 cm. The patient has the metabolic syndrome as defined by the National Cholesterol Education Program. The metabolic syndrome is associated with a 5-9 fold increase in the risk for developing type 2 diabetes and a 2-3 fold increase risk in cardiovascular mortality. The patient is given telmisartan (Micardis®) at an oral dose of 80 mg/day for treatment of the metabolic syndrome. After two weeks of telmisartan therapy, the patient no longer meets the diagnostic criteria of the metabolic syndrome and her blood pressure is reduced to 130/69 mmHg, the fasting glucose is normalized to 105 mg/dl, and the fasting triglyceride level is reduced to 115 mg/dl. Clinical examination reveals no evidence of any increase in fluid retention, peripheral edema, pulmonary edema, or congestive heart failure. The telmisartan (Micardis®) therapy is continued according to the judgment of the clinician in order to prevent recurrence of the metabolic syndrome and prevent development of type 2 diabetes.

Example 6

A Clinical Trial Using a PPARgamma Activator to Treat Inflammation without Causing Fluid Retention, Edema or Heart Failure A 57 year old female with osteoarthritis and inflammation as judged by elevated C-reactive protein (CRP) levels was selected for therapy. Before administration of telmisartan, the patient had a markedly increased serum CRP level of 7.9 mg/L indicative of active inflammation. The patient is given telmisartan (Micardis®) at an oral dose of 80 mg/day. After 6 weeks of telmisartan therapy, the CRP level is reduced to 4.1 mg/L. After 9 weeks of therapy, the CRP level remains reduced at 3.9 mg/L and symptoms of inflammation and osteoarthritis are stabilized. Clinical examination reveals no evidence of any increase in fluid retention, peripheral edema, pulmonary edema, or congestive heart failure. The telmisartan (Micardis®) therapy is continued according to the judgment of the clinician in order to maintain the improved control of the inflammation.

REFERENCES

Examples of ARBs Encompassed by this Invention

1. Maillard M P, Wurzner G, Nussberger J, Centeno C, Burnier M, Brunner H R. Comparative angiotensin II receptor blockade in healthy volunteers: the importance of dosing. Clin Pharmacol Ther. 2002; 71:68-76.
2. Almansa C, et al. Synthesis and structure-activity relationship of a new series of potent AT1 selective angiotensin II receptor antagonists: 5-(biphenyl-4-ylmethyl)pyrazoles. J Med Chem. 1997; 40:547-58.
3. Almansa C, et al. Diphenylpropionic acids as new AT1 selective angiotensin II antagonists. J Med Chem. 1996; 39:2197-206.
4. Le Bourdonnec B, et al. Synthesis and pharmacological evaluation of new pyrazolidine-3,5-diones as AT1 receptor antagonists. J Med Chem. 2000; 43:2685-97.
5. Almansa C, et al. Diphenylpropionic acids as new AT1 selective angiotensin II antagonists. J Med Chem. 1996; 39:2197-206.
6. Norman N H, et al. 4-(Heteroarylthio)-2-biphenylyltetrazoles as nonpeptide angiotensin II antagonists. J Med Chem. 1995; 38:4670-8.
7. Mederski W W, et al. Non-peptide angiotensin II receptor antagonists: synthesis and biological activity of a series of novel 4,5-dihydro-4-oxo-3H-imidazo[4,5-c]pyridine derivatives. J Med Chem. 1994; 37:1632-45.
8. Dhanoa D S, et al. (Dipropylphenoxy)phenylacetic acids: a new generation of nonpeptide angiotensin II receptor antagonists. J Med Chem. 1993; 36:3738-42.
9. Bernhart C A, et al. A new series of imidazolones: highly specific and potent nonpeptide AT1 angiotensin II receptor antagonists. J Med Chem. 1993; 36:3371-80.
10. Atwal K S, et al. Dihydropyrimidine angiotensin II receptor antagonists. J Med Chem. 1992; 35:4751-63.
11. Lin H S, et al. Nonpeptide angiotensin II receptor antagonists: synthetic and computational chemistry of N-[[4-[2-(2H-tetrazol-5-yl)-1-cycloalken-1-yl]phenyl]methyl]imidazole derivatives and their in vitro activity. J Med Chem. 1992; 35:2658-67.
12. Blankley C J, et al. Synthesis and structure-activity relationships of a novel series of non-peptide angiotensin II receptor binding inhibitors specific for the AT2 subtype. J Med Chem. 1991; 34:3248-60.
13. Buhlmayer P, et al. Nonpeptidic angiotensin II antagonists: synthesis and in vitro activity of a series of novel naphthalene and tetrahydronaphthalene derivatives. J Med Chem. 1991; 34:3105-14.
14. Schmidt B, Schieffer B. Angiotensin II AT1 Receptor Antagonists. Clinical Implications of Active Metabolites. J Med Chem. 2003; 46:2261-70.
15. Le Bourdonnec B, et al. Comparison of 3D structures and AT(1) binding properties of pyrazolidine-3,5-diones and tetrahydropyridazine-3,6-diones with parent antihypertensive drug irbesartan. J Med Chem. 2002; 45:4794-8.
16. Ellingboe J W, et al. Metabolites of the angiotensin II antagonist tasosartan: the importance of a second acidic group. J Med Chem. 1998; 41:4251-60.
17. Ashton W H, et al. Triazolinone biphenylsulfonamide derivatives as orally active angiotensin II antagonists with potent AT1 receptor affinity and enhanced AT2 affinity. J Med Chem. 1994; 37:2808-24.
18. Kubo K, et al. Nonpeptide angiotensin II receptor antagonists. Synthesis and biological activity of benzimidazoles. J Med Chem. 1993; 36:1772-84.
19. De B, et al. Discovery of a novel class of orally active, non-peptide angiotensin II antagonists. J Med Chem. 1992; 35:3714-7.
20. Carini D J, et al. Nonpeptide angiotensin II receptor antagonists: the discovery of a series of N-(biphenylylmethyl)imidazoles as potent, orally active antihypertensives. J Med Chem. 1991; 34:2525-47.

Examples of Insulin-sensitizing Agents with Functionalities that can be Used to Derivitize ARBs 21. Brooks D A, Etgen G J, Rito C J, et al. Design and synthesis of 2-methyl-2-[4-(2-[5-methyl-2-aryloxazol-4-yl]ethoxy)phenoxy]propionic acids: a new class of dual PPARalpha/gamma agonists. J Med Chem. 2001; 44:2061-4.

22. Henke B R, Blanchard S G, Brackeen M F, et al. N-(2-Benzoylphenyl)-L-tyrosine PPARγ agonists. 1. Discovery of a novel series of potent antihyperglycemic and antihyperlipidemic agents. J Med Chem. 1998; 41:5020-36.

23. Cronet P, Petersen J F, Folmer R, et al. Structure of the PPARa and—gamma ligand binding domain in complex with AZ 242; ligand selectivity and agonist activation in the PPAR family. Structure (Camb). 2001; 9:699-706.

Anti-inflammatory Effects of ARBs

24. Wang N, et al. Constitutive activation of peroxisome proliferator-activated receptor-gamma suppresses pro-inflammatory adhesion molecules in human vascular endothelial cells. J Biol Chem. 2002; 277:34176-81.

25. Brasier A R, et al. Angiotensin II induces gene transcription through cell-type-dependent effects on the nuclear factor-kappaB (NF-kappaB) transcription factor. Mol Cell Biochem. 2000; 212:155-69.

26. Miyajima A, et al. Angiotensin II type I antagonist prevents pulmonary metastasis of murine renal cancer by inhibiting tumor angiogenesis. Cancer Res. 2002; 62:4176-9.

27. Phillips M I, Kagiyama S. Angiotensin II as a pro-inflammatory mediator. Curr Opin Investig Drugs. 2002; 3:569-77.

28. Miyazaki M, et al. Angiotensin II type 1 receptor antagonist, TCV-116, prevents neointima formation in injured arteries in the dog. Jpn J Pharmacol. 1999; 79:455-60.

29. Sasaki K, et al. Evidence for the importance of angiotensin II type 1 receptor in ischemia-induced angiogenesis. J Clin Invest. 2002; 109:603-11.

30. Silvestre J S, et al. Antiangiogenic effect of angiotensin II type 2 receptor in ischemia-induced angiogenesis in mice hindlimb. Circ Res. 2002; 90:1072-9.

31. Tamarat R, et al. Angiotensin II angiogenic effect in vivo involves vascular endothelial growth factor- and inflammation-related pathways. Lab Invest. 2002; 82:747-56.

32. Horiuchi M, et al. Fluvastatin enhances the inhibitory effects of a selective angiotensin II type 1 receptor blocker, valsartan, on vascular neointimal formation. Circulation. 2003; 107:106-12.

Methods claimed in this invention, in part, applies to natural or synthetic PPAR ligands or activators, described in detail in the following issued, allowed, pending or provisional patent applications:

33. U.S. Pat. No. 09/520,208 1,2-Dithiolane Derivatives, pending

34. U.S. Pat. No. 09/684,738 Novel Dithiolane Derivatives

35. U.S. Pat. No. 6,103,742 Pharmaceutical composition

36. U.S. Pat. No. 6,100,403 Production of benzaldehyde compounds

37. U.S. Pat. No. 6,087,385 Flavonoid derivatives

38. U.S. Pat. No. 6,087,384 Apoptosis inhibitor

39. U.S. Pat. No. 6,028,088 Flavonoid derivatives

40. U.S. Pat. No. RE36,575 Pyridine and thiazolidinedione derivatives

41. U.S. Pat. No. 6,022,897 Selective modulators of PPAR(and methods . . .

42. U.S. Pat. No. 6,011,036 Heterocyclic compounds having antidiabetic . . .

43. U.S. Pat. No. 6,011,031 Azolidinediones useful for the treatment of diabetes . . .

44. U.S. Pat. No. 6,008,237 Arylthiazolidinedione derivatives

45. U.S. Pat. No. 5,990,139 Thiazolidinedione derivatives or salts there of and . . .

46. U.S. Pat. No. 5,985,884 Heterocyclic compounds, process for their preparation . . .

47. U.S. Pat. No. 5,977,365 Heterocyclic compound having anti-diabetic activity

48. U.S. Pat. No. 5,972,970 Oxazolidinedione derivatives, their production and use 49. U.S. Pat. No. 5,972,959 Oxime derivatives, their preparation and therapeutic use 50. U.S. Pat. No. 5,965,589 Thiazolidinedione derivatives, their production and use 51. U.S. Pat. No. 5,962,470 Heterocyclic compounds having anti-diabetic activity . . .

52. U.S. Pat. No. 5,952,509 Production of benzaldehyde compounds

53. U.S. Pat. No. 5,965,584 Pharmaceutical composition

54. U.S. Pat. No. 5,952,356 Pharmaceutical composition

55. U.S. Pat. No. 5,939,442 Modulations of PPAR(, and methods for the use thereof 56. U.S. Pat. No. 5,932,601 Oxazolidinedione derivatives, their production and use 57. U.S. Pat. No. 5,925,656 Compounds having antidiabetic, hypolipidemic . . .

58. U.S. Pat. No. 5,919,782 Heterocyclic compounds having antidiabetic . . .

59. U.S. Pat. No. 5,910,592 Substituted thiazolidinedione derivatives

60. U.S. Pat. No. 5,902,726 Activators of the nuclear orphan receptor PPAR(

61. U.S. Pat. No. 5,889,032 Heterocyclic compounds having antidiabetic . . .

62. U.S. Pat. No. 5,889,025 Antidiabetic compounds having hypolipidaemic . . .

63. U.S. Pat. No. 5,886,014 Benzimidazole derivatives, their preparation . . .

64. U.S. Pat. No. 5,885,997 Heterocyclic compounds, process for their preparation . . .

65. U.S. Pat. No. 5,869,495 Heterocyclic compounds as pharmaceutical

66. U.S. Pat. No. 5,859,051 Antidiabetic agents

67. U.S. Pat. No. 5,847,008 Method of treating diabetes and related disease states 68. U.S. Pat. No. 5,843,970 Thiazolidine derivatives for the treatment of hypertension 69. U.S. Pat. No. 5,834,501 Heterocyclic compounds having anti-diabetic activity . . .

70. U.S. Pat. No. 5,827,865 Heterocyclic compounds as pharmaceutical

71. U.S. Pat. No. 5,824,694 Thiazolidine derivatives for the treatment of psoriasis 72. U.S. Pat. No. 5,811,439 Thiazolidinedione derivatives, method for preparing . . .

73. U.S. Pat. No. 5,801,173 Heterocyclic compounds having antidiabetic . . .

74. U.S. Pat. No. 5,741,803 Substituted thiazolidinedionle derivatives

75. U.S. Pat. No. 5,693,651 Quinoline derivatives

76. U.S. Pat. No. 5,506,245 Thiazolidinedione compounds

77. U.S. Pat. No. 6,150,371 Method for preventing and for treating autoimmune . . .
78. WO 01/12612 Benzoic acid derivatives for the treatment of diabetes . . .
79. WO 98/57941 New thiazolidinedione, oxazolidinedione . . .
80. WO 01/00603 Thiazole and oxazole derivatives . . .
81. WO 97/25042 Use of an antagonist of PPAR-alpha and PPAR-gamma . . .
82. WO 98/05331 Prevention or treatment of type 2 diabetes or cardiovascular . . .
83. WO 97/28137 Heterocyclic derivatives as antidiabetic and antiobesity . . .
84. WO 00/27832 PPARγ ligands
85. WO 01/21602 Oxa- and thiazole derivatives . . .
86. WO 01/34094 Novel compounds to treat diabetes . . .
87. WO 99/62870 New 3-aryl-2-hydroxypropionic acid . . .
88. WO 99/62871 New 3-aryl-2-hydroxypropionic acid . . .
89. WO 99/62872 New 3-aryl-2-hydroxypropionic acid . . .
90. U.S. Pat. No. 5,864,043 Benzimidazoles, medicaments . . .
91. U.S. Pat. No. 5,684,029 Benzimidazoles, pharmaceutical compositions . . .
92. U.S. Pat. No. 5,614,519 (1-(2,3 or 4-N-morpholinoalkyl)-imidazol-4-yl)-benizimidazol-1-yl-methyl]-biphenyls useful as angiotensin-II antagonists
93. U.S. Pat. No. 5,602,127 (Alkanesultam-1-yl)-benzimidazol-1-yl)-1yl)-methyl-biphenyls useful as angiotensin-II antagonists
94. U.S. Pat. No. 5,594,003 Tetrahydroimidazo[1,2-a]pyridin-2-yl-(benzimidazol-1-yl)-methyl-biph enyls useful as angiotensin-II antagonists
95. U.S. Pat. No. 5,591,762 Benzimidazoles useful as angiotensin-11 antagonists
96. U.S. Pat. No. 5,587,393 Benzimidazoles, pharmaceutical compositions . . .
97. U.S. Pat. No. 5,565,469 Benzimidazoles and pharmaceutical compositions
98. U.S. Pat. No. 5,541,229 Benzimidazoles and medicaments
99. U.S. Pat. No. 6,355,808 Benzimidazole compounds, their production and use
100. U.S. Pat. No. 6,232,334 Benzimidazole derivatives, their production and use
101. U.S. Pat. No. 6,004,989 Benzimidazole derivatives, their production and use
102. U.S. Pat. No. 5,962,491 Benzimidazole derivatives and use thereof
103. U.S. Pat. No. 5,883,111 Heterocyclic compounds and their use as angiotensin . . .
104. U.S. Pat. No. 5,736,555 Heterocyclic compounds and their use as angiotensin . . .
105. U.S. Pat. No. 5,705,517 Benzimidazole derivatives and use thereof
106. U.S. Pat. No. 5,703,110 Benzimidazole derivatives, their production and use
107. U.S. Pat. No. 5,583,141 Heterocyclic compounds and their use as angiotensin . . .
108. U.S. Pat. No. 5,500,427 Cyclic compounds and their use
109. U.S. Pat. No. 5,496,835 Heterocyclic compounds having angiotensin II . . .
110. U.S. Pat. No. 6,160,000 Antidiabetic agents based on aryl and heteroarylacetic acids
111. U.S. Pat. No. 6,113,907 Pharmaceutical grade St. John's Wort
112. U.S. Pat. No. 6,090,839 Antidiabetic agents
113. U.S. Pat. No. 6,090,836 Benzisoxazole-derived antidiabetic compounds
114. U.S. Pat. No. 6,020,382 Method of treating diabetes and related disease states
115. U.S. Pat. No. 5,958,942 Tricyclic nitrogen ring compounds, their production and use
116. U.S. Pat. No. 5,859,051 Antidiabetic agents
117. U.S. Pat. No. 5,847,008 Method of treating diabetes and related disease states
118. U.S. Pat. No. 5,843,172 Porous medicated stent
119. U.S. Pat. No. 5,663,187 Treatment of atherosclerosis with angiotensin II receptor blocking imidazoles
120. U.S. Pat. No. 5,663,186 Treatment of atherosclerosis with angiotensin II receptor blocking imidazoles
121. U.S. Pat. No. 6,160,000 Antidiabetic agents based on aryl and heteroarylacetic acids\
122. U.S. Pat. No. 6,479,524 Substituted aryl and heteroaryl derivatives . . .
123. U.S. Pat. No. 6,476,023 Aromatic heterocyclic compounds as anti-inflammatory agents
124. U.S. Pat. No. 6,469,039 Disubstituted bicyclic heterocycles . . .
125. U.S. Pat. No. 6,451,832 Benzimidazoles with antithrombotic activity
126. U.S. Pat. No. 6,414,008 Disubstituted bicyclic heterocycles . . .
127. U.S. Pat. No. 6,372,773 Aromatic heterocyclic compounds as antiinflammatory agents
128. U.S. Pat. No. 6,358,945 Compounds useful as anti-inflammatory agents
129. U.S. Pat. No. 6,333,325 Method of treating cytokine mediated diseases or conditions
130. U.S. Pat. No. 6,329,415 Aromatic heterocyclic compounds as antiinflammatory agents
131. U.S. Pat. No. 6,150,371 Method for preventing and for treating autoimmune disease
132. U.S. Pat. No. 6,117,893 Heterocyclic compounds having anti-diabetic activity . . .
133. U.S. Pat. No. 6,414,002 Substituted acid derivatives useful as antidiabetic and antiobesity agents . . .
134. U.S. Pat. No. 6,432,996 Pharmaceutical composition
135. U.S. Pat. No. 6,432,993 Substituted fused heterocyclic compound (rivoglitazone) . . .
136. U.S. Pat. No. 6,486,188 Method of treatment for cardiovascular complications
137. U.S. Pat. No. 6,420,405 Pharmaceutical composition for angiotensin II-mediated . . .
138. U.S. Pat. No. 6,468,996 Substituted hetero-polycyclic compounds as PPARα/PPARγ . . .
139. U.S. Pat. No. 6,432,996 Pharmaceutical composition
140. U.S. Pat. No. 6,355,808 Benzimidazole compounds, their production and use
141. U.S. Pat. No. 6,348,481 Pharmaceutical composition for angiotensin II-mediated
142. U.S. Pat. No. 6,232,334 Benzimidazole derivatives, their production and use
143. U.S. Pat. No. 6,228,874 Pharmaceutical composition for angiotensin II-mediated . . .
144. U.S. Pat. No. 6,100,252 Heterocyclic compounds and their use as angiotensin antagonists
145. U.S. Pat. No. 5,958,961 Pharmaceutical composition for angiotensin II-mediated diseases 146. U.S. Pat. No. 5,639,773 Ocular hypotensive agent
147. U.S. Pat. No. 6,355,808 Benzimidazole compounds, their production and use
148. U.S. Pat. No. 6,232,334 Benzimidazole derivatives, their production and use
149. U.S. Pat. No. 5,463,073 Thienoimidazole derivatives, their production and use
150. U.S. Pat. No. 5,401,764 Benzimidazole derivative compositions and medical use thereof
151. U.S. Pat. No. 5,389,641 Fused heterocyclic compounds, having angiotensin II antagonistic activity
152. U.S. Pat. No. 5,354,766 Compound and salts thereof which antagonize angiotensin II
153. U.S. Pat. No. 5,328,919 Pivaloyloxymethyl 2-ethoxy-1-[[2'-(1H-tetrazol-5-yl)biphenyl-4-yl]benzimidazole-7-carboxylate or a pharmaceutically acceptable salt thereof . . .
154. U.S. Pat. No. 5,284,661 Fused thiophene derivatives, their production and use
155. U.S. Pat. No. 5,250,554 Benzimidazole derivatives useful as angiotensin II inhibitors
156. U.S. Pat. No. 5,243,054 Compound which is angiotensin II antagonist
157. U.S. Pat. No. 5,196,444 1-(cyclohexyloxycarbonyloxy)ethyl 2-ethoxy-1-[[2'-(1H-tetrazol-5-yl)biphenyl-4-yl] methyl]benzimidazole-7-c arboxylate . . .
158. U.S. Pat. No. 5,162,326 Pyrimidinedione derivatives, their production and use
159. U.S. Pat. No. 5,128,356 Benzimidazole derivatives and their use
160. U.S. Pat. No. 6,200,995 PPARγ modulators (Tularik)
161. U.S. Prov. Pat. No. 60/283,774 Optimized ligands for PPARs
162. U.S. Prov. Pat. No. 60/189,514 Novel Antioxidants
163. U.S. Prov. Pat. No. 60/402,425 Identification and uses of novel PPAR ligands that do not cause fluid retention The above-named patents contain the description of compounds that can be utilized in the practice of this invention. Consequently said compounds are covered according to the claims of this invention.

All publications, patents and patent publications mentioned in this specification are herein incorporated by reference into the specification in their entirety for all purposes.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

The foregoing is offered primarily for purposes of illustration. It will be readily apparent to those of ordinary skill in the art that the operating conditions, materials, procedural steps and other parameters of the invention described herein may be further modified or substituted in various ways without departing from the spirit and scope of the invention. For example, the invention has been described with human patients as the usual recipient, but veterinary use is also contemplated. Thus, the preceding description of the invention should not be viewed as limiting but as merely exemplary.

What is claimed is:

1. A method for decreasing an incidence of a new onset of type 2 diabetes mellitus, in a mammal by administering to the mammal in need thereof, a increase the activity of a peroxisome proliferators activated receptor (PPAR) gamma.

2. The method of claim 1 wherein the decreasing the incidence of the new onset of type 2 diabetes mellitus, does not cause, promote, or aggravate fluid retention, peripheral edema, pulmonary edema, or congestive heart failure in the mammal.

3. The method of claim 1 wherein the telmisartan, is administered in a pharmaceutically acceptable form.

4. The method of claim 1 wherein the telmisartan, is formulated for oral administration.

5. The method of claim 1 wherein the telmisartan, is formulated for topical administration.

6. The method of claim 4 wherein a total effective daily orally administered dose is selected from the range of about 20 mg to about 1000 mg.

7. The method of claim 4 wherein the total effective daily orally administered dose is selected from the range of about 0.05 to 100 mg/kg body weight.

8. The method of claim 1 wherein the mammal is a human child, adolescent or adult.

* * * * *

UNITED STATES PATENT AND TRADEMARK OFFICE
CERTIFICATE OF CORRECTION

PATENT NO. : 7,232,828 B2
APPLICATION NO. : 10/627372
DATED : June 19, 2007
INVENTOR(S) : Harrihar A. Pershadsingh It is certified that error appears in the above-identified patent and that said Letters Patent is hereby corrected as shown below:

In Claim 1, column 48, line 21, please replace "mellitus," with --mellitus--.

In Claim 1, column 48, line 22, please replace ", a increase" with --, a therapeutically effective amount of telmisartan sufficient to increase--.

In Claim 1, column 48, line 23, please replace "proliferators" with --proliferator--.

In Claim 2, column 48, line 25, please replace "mellitus," with --mellitus--.

In Claim 3, column 48, line 29, please replace "telmisartan," with --telmisartan--.

In Claim 4, column 48, line 31, please replace "telmisartan," with --telmisartan--.

In Claim 5, column 48, line 33, please replace "telmisartan," with --telmisartan--.

UNITED STATES PATENT AND TRADEMARK OFFICE
CERTIFICATE OF CORRECTION

PATENT NO. : 7,232,828 B2
APPLICATION NO. : 10/627372
DATED : June 19, 2007
INVENTOR(S) : Harrihar A. Pershadsingh It is certified that error appears in the above-identified patent and that said Letters Patent is hereby corrected as shown below:

In Claim 7, column 48, line 38, please replace "the total effective" with --a total effective--.

Signed and Sealed this

Twenty-seventh Day of May, 2008

JON W. DUDAS
*Director of the United States Patent and Trademark Office*